United States Patent [19]
Ballinger et al.

[11] Patent Number: 5,741,664
[45] Date of Patent: Apr. 21, 1998

[54] SUBTILISIN VARIANTS CAPABLE OF CLEAVING SUBSTRATES CONTAINING DIBASIC RESIDUES

[75] Inventors: Marcus D. Ballinger; James A. Wells, both of Burlingame, Calif.

[73] Assignee: Genentech, Inc., South San Francisco, Calif.

[21] Appl. No.: 460,343

[22] Filed: Jun. 1, 1995

Related U.S. Application Data

[63] Continuation of Ser. No. 398,028, Mar. 3, 1995.
[51] Int. Cl.$^6$ .............................. C12P 21/00; C12N 9/54; C12N 9/56; C12N 15/57
[52] U.S. Cl. .................... 435/68.1; 435/69.1; 435/172.3; 435/221; 435/222; 435/252.3; 435/252.31; 435/320.1; 536/23.2
[58] Field of Search .................... 435/68.1, 69.1, 435/172.3, 221, 222, 252.3, 252.31, 320.1; 536/23.2

[56] References Cited

U.S. PATENT DOCUMENTS

| | | | |
|---|---|---|---|
| 4,760,025 | 7/1988 | Estell et al. | 435/222 |
| 5,371,008 | 12/1994 | Carter et al. | 435/222 |

FOREIGN PATENT DOCUMENTS

| | | |
|---|---|---|
| 251446 | 1/1988 | European Pat. Off. |
| 316748 | 5/1989 | European Pat. Off. |
| 405901 | 1/1991 | European Pat. Off. |
| 0130756 | 6/1991 | European Pat. Off. |
| WO 91/11454 | 8/1991 | WIPO. |
| WO 92/02615 | 2/1992 | WIPO. |
| WO 95/30010 | 11/1995 | WIPO. |

OTHER PUBLICATIONS

Bode et al., "Refined 1.2 A crystal structure of the complex formed between subtilisin Carlsberg and the inhibitor eglin c. Molecular structure of eglin and its detailed interaction with subtilisin" *EMBO Journal* 5(4):813–818 (1986).

Brenner et al., "Structural and enzymatic characterization of a purified prohormone-processing enzyme: Secreted, soluble Kex2 protease" *Proc. Natl. Acad. Sci. USA* 89:922–926 (1992).

Bresnahan, P. A. et al., "Human fur gene encodes a yeas kex2–like endoprotease that cleaves pro–β–NGF in vivo" *Journal of Cell Biology* 111(6, Pt 2):2851–2859 (1990).

Carter et al., "Engineering Subtilisin BPN' for Site–Specific Proteolysis" *Proteins: Struct. Funct., Genet.* 6:240–248 (1989).

Creemers et al., "Modulation of Furin–Mediated Proprotein Processing Activity by Site–directed Mutagenesis" *The Journal of Biological Chemistry* 268(29):21826–21834 (1993).

Drenth et al., "Subtilisin Novo; The Three–Dimensional Structure and Its Comparison with Subtilisin BPN'" *European Journal of Biochemistry* 26:177–181 (1972).

(List continued on next page.)

*Primary Examiner*—Robert A. Wax
*Assistant Examiner*—William W. Moore
*Attorney, Agent, or Firm*—Jeffrey S. Kubinec

[57] ABSTRACT

The bacterial serine protease, subtilisin BPN', has been mutated so that it will efficiently and selectively cleave substrates containing dibasic residues. A combination mutant, where Asn 62 was changed to Asp and Gly 166 was changed to Asp (N62D/G166D), had a larger than additive shift in specificity toward dibasic substrates. Suitable substrates of the variant subtilisin were revealed by sorting a library of phage particles (substrate phage) containing five contiguous randomized residues. This method identified a particularly good substrate, Asn-Leu-Met-Arg-Lys-, that was selectively cleaved in the context of a fusion protein by the N62D/G166D subtilisin variant. Accordingly, this variant subtilisin may be useful for cleaving fusion proteins with dibasic substrate linkers and processing hormones or other proteins (in vitro or in vivo) that contain dibasic cleavage sites.

11 Claims, 19 Drawing Sheets

OTHER PUBLICATIONS

Eder et al., "Hydrolysis of Small Peptide Substrates Parallels Binding of Chymotrypsin Inhibitor 2 for Mutants of Subtilisn BPN'" *Federation of European Biochemical Societies* 335(3):349–352 (1993).

Forsberg et al., "An Evaluation of Different Enzymatic Cleavage Methods for Recombination Fusion Proteins, Applied on Des(1–3) Insulin–Like Growth Factor I" *Journal of Protein Chemistry* 11(2):201–211 (1992).

Graf et al., "Electrostatic Complementarity Within the Substrate–Binding Pocket of Trypsin" *Proc. Natl. Acad. Sci.* 85:4961–4965 (1988).

Hedstrom et al., "Converting Trypsin to Chymotrypsin: The Role of Surface Loops" *Science*, 255(5049):1249–1253 (1992).

Hosaka et al., "Arg–X–Lys/Arg–Arg Motif as a Signal for Precursor Cleavage Catalyzed by Furin within the Constitutive Secretory Pathway" *Journal of Biological Chemistry* 266(19):12127–12130 (1991).

Hwang et al., "Why ION Pair Reversal by Protein Engineering is Unlikely to Succeed" *Nature* 334:270–272 (1988).

Knauf et al., "Relationship of Effective Molecular Size to Systemic Clearance in Rats of Reconbinant Interleukin–2 Chemically Modified with Water Soluble Polymers" *The Journal of Biolgical Chemistry* 29(Oct. 15):15064–15070 (1988).

Kraut, Joseph, "Serine Proteases: Structure and Mechanism of Catalysis" *Ann. Rev. Biochem.* 46:331–358 (1977).

Lipkind et al., "Molecular Modeling of the Substrate Specificity of Prohormone Convertases SPC2 and SPC3" *The Journal of Biological Chemistry* 270(22):13277–13284 (1995).

Matthews et al., "A Survey of Furin Substrate Specificity Using Substrate Phage Display" *Protein Science* 3:1197–1205 (1994).

Matthews et al., "X–ray Crystallographic Study of Boronic Acid Adducts with Subtilisin BPN' (Novo)" *Journal of Biological Chemistry* 250(18):7120–7126 (1975).

McPhalen et al., "Structural Comparison of Two Serine Proteinase–Protein Inhibitor Complexes: Eglin–C–Subtilisin Carlsberg and CI–2–Subtilisin Novo" *Biochemistry* 27:6582–6598 (1988).

Philipp et al., "Kinetics of Subtilisin and Thiolsubtilisin" *Molecular and Cellular Biochemistry* 51(5):5–32 (1983).

Poulos et al., "Polypeptide Halomethyl Ketones Bind to Serine Proteases as Analogs of the Tetrahedral Intermediate" *The Journal of Biological Chemistry* pp. 1097–1103 (1975).

Rheinnecker et al., "Engineering a Novel Specificity in Subtilisin BPN'" *Biochemistry* 32(5):1199–1203 (1993).

Rheinnecker et al., "Variants of Subtilisin BPN' with Altered Specificity Profiles" *Biochemistry* 33:221–225 (1994).

Robertus et al., "Subtilisin; a Stereochemical Mechanism Involving Transition–State Stabilization" *Biochemistry* 11:4293–4303 (1972).

Robertus et al., "An X–Ray Crystallographic Study of the Binder of Peptide Choloromethyl Ketone Inhibitors to Subtilisin BPN'" *Biochemistry* 11(13):2439–2449 (1972).

Russell et al., "Rational modification of enzyme catalysis by engineering surface charge" *Nature* 328:496–500 (1987).

Siezen et al., "Homology Modelling and Protein Engineering Strategy of Subtilases, the Family of Subtilisin–Like Serine Proteinases" *Protein Engineering* 4(7):719–737 (1991).

Siezen et al., "Homology Modelling of the Catalytic Domain of Human Furin, a Model for the Eukaryotic Subtilisin–Like Proprotein Convertases" *FEBS Letter* pp. 255–266 (1994).

Smeekens, Steven P., "Processing of Protein Precursors by a Novel Family of Subtilisin–Related Mammalian Endoproteases" *Bio/Technology* 11:182–186 (1993).

Stauffer et al., "The Effect on Subtilisin Actvity of Oxidizing a Methionine Residue" *The Journal of Biological Chemistry* 244(19):5333–5338 (1969).

Steiner et al., "The New Enzymology of Precursor Processing Endoproteases" *Journal of Biological Chemistry* 267(33):23435–23438 (1992).

Stennicke et al., "Effects of introduced aspartic and glutamic acid residues on the P'$_1$ substrate specificity, pH dependence and stability of carboxypeptidase Y" *Protein Engineering* 7(7):911–916 (1994).

Svendsen, I., "Chemical Modifications of The Subtilisins With Specific Reference to the Binding of Large Substrates. A Review." *Carlsberg Rs. Commun.* 41(5):237–291 (1976).

Wells et al., "Cloning, sequencing, and secretion of *Bacillus amyloliquefaciens* subtilisin in *Bacillus subtilis*" *Nucleic Acids Research* 11(22):7911–7929 (1983).

Wells et al., "Designing substrate specificity by protein engineering of electrostatic interactions" *Proc. Natl. Acad. Sci. USA* 84:1219–1223 (1987).

Wise et al., "Expression of a human proprotein processing enzyme: correct cleavage of the von Willebrand factor precursor at a paired basic amino acid site" *Proc. Natl. Acad. Sci. USA* 87:9378–9382 (1990).

Wright et al., "Structure of Subtilisin BPN' at 2–5 A Resolution" *Nature* 221:235–242 (1969).

Estell et al., "Probing Steric and Hydrophobic Effects on Enzyme–Substrate Interactions by Protein Engineering" *Science* 233:659–663 (1986).

Graycar et al., "Altering the Proteolytic Activity of Subtilisin through Protein Engineering" *Annals of the New York Academy of Sciences* 672:71–79 (1992).

Nakayama et al., "Consensus Sequence for Precursor Processing at Mono–arginyl Sites" *Journal of Biological Chemistry* 267:16335–16340 (1992).

Wells et al., "Recruitment of Substrate–specificity Properties from One Enzyme Into a Related One by Protein Engineering" *Proc. Natl. Acad. Sci. USA* 84:5167–5171 (1987).

Wells et al., "Subtilisin: An Enzyme Made for Engineering" *J. Cell. Biochem.* (abstract B7–012) Suppl. 19B:233 (1995).

```
                         nspBII    claI/bspl06        ahaIII/draI
505 GTA GCG GTT ATC GAC AGC GGT ATC GAT TCT TCT CAT CCT GAT CTA AAG GTA GCA GGC GGA GCC AGC ATG GTT CCT TCT GAA
    CAT CGC CAA TAG CTG TCG CCA TAG CTA AGA AGA GTA GGA CTA GAT TTC CAT CGT CCG CCT CGG TCG TAC CAA GGA AGA CTT
    Val Ala Val Ile Asp Ser Gly Ile Asp Ser Ser His Pro Asp Leu Lys Val Ala Gly Gly Ala Ser Met Val Pro Ser Glu
                30                            40                             50 naeI
                                                                          cfr10I
586 ACA AAT CCT TTC CAA GAC AAC GAC TCT CAC GGA ACT CAC GTT GCC GGC ACA GTT GCG GCT CTT AAT AAC TCA ATC GGT GTA
    TGT TTA GGA AAG GTT CTG TTG CTG AGA GTG CCT TGA GTG CAA CGG CCG TGT CAA CGC CGA GAA TTA TTG AGT TAG CCA CAT
    Thr Asn Pro Phe Gln Asp Asn Asp Ser His Gly Thr His Val Ala Gly Thr Val Ala Ala Leu Asn Asn Ser Ile Gly Val
                    60                             70                             80 eaeI        pvuII
                                                                           cfrI        nspBII
667 TTA GGC GTT GCG CCA AGC GCA TCA CTT TAC GCT GTA AAA GTT CTC GGT GCT GAC GGT TCC GGC CAA TAC AGC TGG ATC ATT
    AAT CCG CAA CGC GGT TCG CGT AGT GAA ATG CGA CAT TTT CAA GAG CCA CGA CTG CCA AGG CCG GTT ATG TCG ACC TAG TAA
    Leu Gly Val Ala Pro Ser Ala Ser Leu Tyr Ala Val Lys Val Leu Gly Ala Asp Gly Ser Gly Gln Tyr Ser Trp Ile Ile
                    90                             100 pvuI/bspCI                                                                          ahaII/draI
                   mcrI
748 AAC GGA ATC GAG TGG GCG ATC GCA AAC AAT ATG GAC GTT AAC AGC CTC ATT GGC GGA CCT TCT GGT TCT GCT TTA
    TTG CCT TAG CTC ACC CGC TAG CGT TTG TTA TAC CTG CAA TTG TCG GAG TAA CCG CCT GGA AGA CCA AGA CGA AAT
    Asn Gly Ile Glu Trp Ala Ile Ala Asn Asn Met Asp Val Asn Ser Leu Ile Gly Gly Pro Ser Gly Ser Ala Ala Leu
                   110                            120                            130 salI
                      hinlI/acyI                                                              hincII/hindII
                      ahaII/bsaHI                cfr10I                                       accI
829 AAA GCG GCA GTT GAT AAA GCC GTT GCA TCC GGC GTA GTC GTT GCG GCA GCC GGT AAC GAA GGC ACT TCC GGC AGC TCG
    TTT CGC CGT CAA CTA TTT CGG CAA CGT AGG CCG CAT CAG CAA CGC CGT CGG CCA TTG CTT CCG TGA AGG CCG TCG AGC
    Lys Ala Ala Val Asp Lys Ala Val Ala Ser Gly Val Val Ala Ala Ala Gly Asn Glu Gly Thr Ser Gly Ser Ser
                   140                            150                            160 haeII    hincII/hindII
910 TCG ACA GTG GAC TAC CCT GGA AAA TAC ATG GGC GCT GTT GAC AGC GTA CAA AGA GCA TCT TTC
    AGC TGT CAC CTG ATG GGA CCT TTT ATG TAC CCG CGA CAA CTG TCG CAT GTT TCT CGT AGA AAG
    Ser Thr Val Asp Tyr Pro Gly Lys Tyr Met Gly Ala Val Asp Ser Val Gln Arg Ala Ser Phe
                   170                            180
```

```
                    ppuMI
                    ecoO109I/draII                    hgiCI
                                                      banI
 991 TCA AGC GTA GGA CCT GAG CTT GAT GTC GCA CCT GGC GTA TCT ATC CAA AGC ACG CTT CCT GGA AAC AAA TAC GGG GCG
     AGT TCG CAT CCT GGA CTC GAA CTA CAG CGT GGA CCG CAT GCA TAG ATA GTT TCG TGC GAA GGA CCT TTG TTT ATG CCC CGC
     Ser Ser Val Gly Pro Glu Leu Asp Val Met Ala Pro Gly Val Ser Ile Gln Ser Thr Leu Pro Gly Asn Lys Tyr Gly Ala
     190                                             200                                             210 kpnI
           hgiCI
           banI
           asp718
           acc65I                                bglI bsrBI
1072 TAC AAC GGT ACC TCA ATG GCA TCT CCG CAC GTT GCC GGA CCT GCT GCT TTG ATT CTT TCT AAG CAC CCG AAC TGG ACA AAC
     ATG TTG CCA TGG AGT TAC CGT AGA GGC GTG CAA CGG CCT CGC CGA CGA AAC TAA GAA AGA TTC GTG GGC TTG ACC TGT TTG
     Tyr Asn Gly Thr Ser Met Ala Ser Pro His Val Ala Gly Pro Ala Ala Leu Ile Leu Ser Lys His Pro Asn Trp Thr Asn
                                 220                                             230                         240 bclI[dam-]
1153 ACT CAA GTC CGC CGC AGC AGT TTA GAA AAC ACC ACA AAA CTT GGT GAT TCT AGA AAG ATG TAT GGA AAA GGG CTG ATC AAC GTA
     TGA GTT CAG GCG GCG TCG TCA AAT CTT TTG TGG TGT TTT GAA CCA CTA AGA TCT TTC TAC ATA CCT TTT CCC GAC TAG TTG CAT
     Thr Gln Val Arg Ser Ser Ser Leu Glu Asn Thr Thr Lys Leu Gly Asp Ser Arg Lys Met Tyr Gly Lys Gly Leu Ile Asn Val
                             250                                             260                                 270 nspI
                                                      styI                nspHI              bsrBI
                                                      cfr10I
1234 CAG GCG GCA GCT CAG TAA AACATAAAA AACCGGCCTT GGCCCCGCCG GTTTTTTATT ATTTTTCTTC CTCCGCATGT TCAATCCGCT
     GTC CGC CGT CGA GTC ATT TTGTATTTT TTGGCCGGAA CCGGGGCGGC CAAAAAATAA TAAAAAGAAG GAGGCGTACA AGTTAGGCGA
     Gln Ala Ala Ala Gln Oc*
            apoI                                hincII/hindII                               eaeI
                                                                                            cfrI              esp3I
1321 CCATAATCGA CGGATGGCTC CCTCTGAAAC TTTTAACGAG AAACGGCGGG TTGACCCGGC TCAGTCCCGT AACGGCCAAG TCCTGAAACG TCTCAATCGC
     GGTATTAGCT GCCTACCGAG GGAGACTTTG AAATTGCTC TTTGCCGCCC AACTGGGCCG AGTCAGGGCA TTGCCGGTTC AGGACTTTGC AGAGTTAGCG
```

FIG. 6C

```
                                                                                                   mroI
                                                                                                   bspMII
                                                                                                   bspEI[dam-]
                                                                                                   bsaWI
                                                                                                   accIII[dam-]
                                                                                     esp3I bsmI    bstYI/xhoII
              bsaWI                         mcrI                                                   bamHI              psp1406I
1421 CGCTTCCCGG TTTCCGGTCA GCTCAATGCC GTAACGGTCG GCGGCGTATT CCTGATACCG GGAGACGGCA TTCGTAATCG GATCCGGAAA TTGTAAACGT
     GCGAAGGGCC AAAGGCCAGT CGAGTTACGG CATTGCCAGC CGCCGCATAA GGACTATGGC CCTCTGCCGT AAGCATTAGC CTAGGCCTTT AACATTTGCA sspI        apoI
1521 TAATATTTTG TTAAAATTCG CGTTAAATTT AGCTCATTTT TTGTTAAATC GGCCGAAATC GGCAAAATCC CTTATAAATC AAAAGAATAG
     ATTATAAAAC AATTTTAAGC GCAATTTAAA TCGAGTAAAA AACAATTTAG CCGGCTTTAG CCGTTTTAGG GAATATTTAG TTTTCTTATC drdI
1621 ACCGAGATAG GGTTGAGTGT TGTTCCAGTT TGGAACAAGA GTCCACTATT AAAGAACGTG GACTCCAACG TCAAAGGGCG AAAAACCGTC TATCAGGGCT
     TGGCTCTATC CCAACTCACA ACAAGGTCAA ACCTTGTTCT CAGGTGATAA TTTCTTGCAC CTGAGGTTGC AGTTTCCCGC TTTTTGGCAG ATAGTCCCGA hgiJII
                                                        hgiCI                                      bsp1286
                                                        banI                                       bmyI
              bsaAI                                                                                banII
              draIII
1721 ATGGCCCACT ACGTGGAACCA TCACCCTAAT CAAGTTTTTT GGGGTCGAGG TGCCGTAAAG CACTAAATCG GAACCCTAAA GGGAGCCCCC GATTTAGAGC
     TACCGGGTGA TGCACTTGGT AGTGGGATTA GTTCAAAAAA CCCCAGCTCC ACGGCATTTC GTGATTTAGC CTTGGGATTT CCCTCGGGGG CTAAATCTCG naeI
              cfr10I                                          bsrBI          haeII
                                                              hgiCI
1821 TTGACGGGGA AAGCCGGCGA ACGTGGCGAG AAAGGAAGGG AAGAAAGCGA AAGGAGCGGG CGCTAGGGCG CTGGCAAGTG TAGCGGTCAC GCTGCGGTA
     AACTGCCCCT TTCGGCCGCT TGCACCGCTC TTTCCTTCCC TTCTTTCGCT TTCCTCGCCC GCGATCCCGC GACCGTTCAC ATCGCCAGTG CGACGCGCAT
```

FIG. 6D

```
                                                  mroI
                                                  bspMII
                                                  bspEI[dam-]
                                                  bsaWI
                       scfI                       accIII[dam-]              haeI
1921 ACCACCACAC CGGCCGCGCT TAATGCGCCG CTACAGGGCG CGTCCGGATC XGATCCGACG CGAGGCTGGA TGGCCTTCCC CATTATGATT CTTCTCGCTT
     TGGTGGTGTG GCCGGCGCGA ATTACGCGGC GATGTCCCGC GCAGGCCTAG PCTAGGCTGC GCTCCGACCT ACCGGAAGGG GTAATACTAA GAAGAGCGAA haeI                     bspMI
2021 CCGGCGGCAT CGGGATGCCC GCGTTGCAGG CCATGCTGTC CAGGCAGGTA GATGACGACC ATCAGGGACA GCTTCAAGGA TCGCTCGCGG CTCTTACCAG
     GGCCGCCGTA GCCCTACGGG CGCAACGTCC GGTACGACAG GTCCGTCCAT CTACTGCTGG TAGTCCCTGT CGAAGTTCCT AGCGAGCGCC GAGAATGGTC narI
                                                                                                    kasI
                                                                                                    hinII/acyI
                                                                                                    hgiCI
                                                                hgiAI/aspHI                         haeII
                                                                bsp1286                             banI
                                         nspBII                 bsiHKAI                             ahaII/bsaHI
2121 CCTAACTTCG ATCACTGGAC CGCTGATCGT CACGGGCGATT TATGCCGGCT CGGCGAGCAC ATGGAACGGG TTGGCATGGA TTGTAGGCGC CGCCCTATAC
     GGATTGAAGC TAGTGACCTG GCGACTAGCA ATACGGCCGA ATACGGCCGA GCCGCTCGTG TACCTTGCCC AACCGTACCT AACATCCGGG GCGGGATATG
                                              bglI                         bmyI hgiCI
                                                                                    naeI  banI
                                                                                    cfr10I                   pflMI
2221 CTTGTCTGCC TCCCCGCGTT GGCTCGCGGT GCATGGAGCC GGGCCACCTC GACCTGAATG GAAGCCGGCG GCACCTCGCT AACGGATTCA CCACTCCAAG
     GAACAGACGG AGGGGCGCAA CCGAGCGCCA CGTACCTCGG CCCGGTGGAG CTGGACTTAC CTTCGGCCGC CGTGGAGCCA TTGCCTAAGT GGTGAGGTTC mstI
                  avill/fspI    styI
                  bsmI          pflMI                                                                gsuI/bpmI
2321 AATTGGAGCC AATCAATTCT TGCGGAGAAC TGTGAATGCG CAAACCAACC CTTGGCAGAA CATATCCATC GCGTCCGCCA TCTCCAGCAG CCGCACGCGG
     TTAACCTCGG TTAGTTAAGA ACGCCTCTTG ACACTTACGC GTTTGGTTGG GAACCGTCTT GTATAGGTAG CGCAGGCGGT AGAGGTCGTC GGCGTGCGCC avaI                                                                      drdI
2421 CGCATCTCGG GCCGCGTTGC TGGCGTTTTT CCATAGGCTC CGCCCCCCTG ACGAGCATCA CAAAAATCGA CGCTCAAGTC AGAGGTGGGC AAACCCGACA
     GCGTAGAGCC CGGCGCAACG ACCGCAAAAA GGTATCCGAG GCGGGGGGAC TGCTCGTAGT GTTTTAGCT GCGAGTTCAG TCTCCACCCG TTTGGGCTGT
```

FIG. 6E

```
                                                                                                      bsaWI
2521  GGACTATAAA GATACCAGGC GTTTCCCCCT GGAAGCTCCC TCGTGCGCTC TCCTGTTCCG ACCCTGCCGC TTACCGGATA CCTGTCCGCC TTTCTCCCTT
      CCTGATATTT CTATGGTCCG CAAAGGGGGA CCTTCGAGGG AGCACGCGAG AGGACAAGGC TGGGACGGCG AATGGCCTAT GGACAGGCGG AAAGAGGGAA haeII            scfI                                                      hgiAI/aspHI
                                                                                                      bsp1286
                                                                                                      bsiHKAI
                                                                                                      bmyI
                                                                                                      apaLI/snoI
                                                                                                      alw44I/snoI
2621  CGGGAAGCGT GGCGCTTTCT CAATGCTCAC GCTGTAGGTA TCTCAGTTCG GTGTAGGTCG TTCGCTCCAA GCTGGGCTGT GTGCACGAAC CCCCCGTTCA
      GCCCTTCGCA CCGCGAAAGA GTTACGAGTG CGACATCCAT AGAGTCAAGC CACATCCAGC AAGCGAGGTT CGACCCGACA CACGTGCTTG GGGGGCAAGT nspBII
            mcrI              bsaWI                                                       alwNI
2721  GCCCGACCGC TGCGCCTTAT CCGGTAACTA TCGTCTTGAG TCCAACCCGG TAAGACACGA CTTATCGCCA CTGGCAGCAG CCACTGGTAA CAGGATTAGC
      CGGGCTGGCG ACGCGGAATA GGCCATTGAT AGCAGAACTC AGGTTGGGCC ATTCTGTGCT GAATAGCGGT GACCGTCGTC GGTGACCATT GTCCTAATCG scfI                                       haeI                                       eco57I
2821  AGAGCGAGGT ATGTAGGCGG TGCTACAGAG TTCTTGAAGT GGTGGCCTAA CTACGGCTAC ACTAGAAGGA CAGTATTTGG TATCTGCGCT CTGCTGAAGC
      TCTCGCTCCA TACATCCGCC ACGATGTCTC AAGAACTTCA CCACCGGATT GATGCCGATG TGATCTTCCT GTCATAAACC ATAGACGCGA GACGACTTCG nspBII
2921  CAGTTACCTT CGGAAAAAGA GTTGGTAGCT CTTGATCCGG CAAAACAAACC ACCGCTGGTA GCGGTGGTTT TTTTGTTTGC AAGCAGCAGA TTACGCGCAG
      GTCAATGGAA GCCTTTTTCT CAACCATCGA GAACTAGGCC GTTTTGTTTGG TGGCGACCAT CGCCACCAAA AAAACAAACG TTCGTCGTCT AATGCGCGTC rcaI
      bstYI/xhoII bstYI/xhoII                                                        bspHI
3021  AAAAAAAGGA TCTCAAGAAG ATCCTTTGAT CTTTTCTACG GGGTCTGACG CTCAGTGGAA CGAAAACTCA CGTTAAGGGA TTTTGGTCAT GAGATTATCA
      TTTTTTTCCT AGAGTTCTTC TAGGAAACTA GAAAAGATGC CCCAGACTGC GAGTCACCTT GCTTTTGAGT GCAATTCCCT AAAACCAGTA CTCTAATAGT ahaIII/draI
      bstYI/xhoII bstYI/xhoII        ahaIII/draI
3121  AAAGGATCT TCACCTAGAT CCTTTTAAAT TAAAAATGAA GTTTTAAATC AATCTAAAGT ATATATGAGT AAACTTGGTC TGACAGTTAC CAATGCTTAA
      TTTTCCTAGA AGTGGATCTA GGAAAATTTA ATTTTTACTT CAAAATTTAG TTAGATTTCA TATATACTCA TTTGAACCAG ACTGTCAATG GTTACGAATT
```

FIG. 6F

```
                    hgiCI                                              eam1105I
                    banI
3221 TCAGTGAGGC ACCTATCTCA GCGATCTGTC TATTTCGTTC ATCCATAGTT GCCTGACTCC CCGTCGTGTA GATAACTACG ATACGGGAGG GCTTACCATC
     AGTCACTCCG TGGATAGAGT CGCTAGACAG ATAAAGCAAG TAGGTATCAA CGGACTGAGG GGCAGCACAT CTATTGATGC TATGCCCTCC CGAATGGTAG bsaI              gsuI/bpmI                           bglI
                                      cfr10I
3321 TGGCCCCAGT GCTGCAATGA TACCGCGAGA CCCACGCTCA CCGGCTCCAG ATTTATCAGC AATAAACCAG CCAGCCGGAA GGGCCGAGCG CAGAAGTGGT
     ACCGGGGTCA CGACGTTACT ATGGCGCTCT GGGTGCGAGT GGCCGAGGTC TAAATAGTCG TTATTTGGTC GGTCGGCCTT CCCGGCTCGC GTCTTCACCA asel/asnI/vspI                                    mstI psp1406I
                                                                                        avill/fspI
3421 CCTGCAACTT TATCCGCCTC CATCCAGTCT ATTAATTGTT GCCGGGAAGC TAGAGTAAGT AGTTCGCCAG TTAATAGTTT GCGCAACGTT GTTGCCATTG
     GGACGTTGAA ATAGGCGGAG GTAGGTCAGA TAATTAACAA CGGCCCTTCG ATCTCATTCA TCAAGCGGTC AATTATCAAA CGCGTTGCAA CAACGGTAAC scfI
     pstI                                                          bsaWI
     bsgI
3521 CTGCAGGCAT CGTGGTGTCA CGCTCGTCGT TTGGTATGGC TTCATTCAGC AGTTCGCCAG TCCGGTTCCC AACGATCAAG GCGAGTTACA TGATCCCCCA TGTTGTGCAA
     GACGTCCGTA GCACCACAGT GCGAGCAGCA AACCATACCG AAGTAAGTCG TCAAGCGGTC AGGCCAAGGG TTGCTAGTTC CGCTCAATGT ACTAGGGGGT ACAACACGTT pvuI/bspCI              eaeI
                         mcrI                    cfrI
3621 AAAAGGGGTT AGCTCCTTCG GTCCTCCGAT CGTTGTCAGA AGTAAGTTGG CCCGAGTGTT ATCACTCATG GTTATGGCAG CACTGCATAA TTCTCTTACT
     TTTTCCCCAA TCGAGGAAGC CAGGAGGCTA GCAACAGTCT TCATTCAACC GGCGTCACAA TAGTGAGTAC CAATACCGTC GTGACGTATT AAGAGAATGA scaI                                                                   hincII/hindII
                                                                                                                  hinlI/acyI
                                                                                               mcrI               ahaII/bsaHI
                                                                                               bcgI
3721 GTCATGCCAT CCGTAAGATG CTTTTCTGTG ACTGGTGAGT ACTCAACCAA GTCATTCTGA GAATAGTGTA TGCGGGCGACC GAGTTGCTCT TGCCCGGGCT
     CAGTACGGTA GGCATTCTAC GAAAAGACAC TGACCACTCA TGAGTTGGTT CAGTAAGACT CTTATCACAT ACGCCCGCTGG CTCAACGAGA ACGGGCCCGA
```

FIG. 6G

```
                                           hgiAI/aspHI
                                           bsp1286
                                           bsiHKAI
                                           bmyI                                                                      bstYI/xhoII
                         ahaIII/draI                  psp1406I                                                                      nspBII
3821 CAACACGGGA TAATACCGCG CCACATAGCA GAACTTTAAA AGTGCTCATC ATTGGAAAAC GTTCTTCGGG GCGAAAACTC TCAAGGATCT TACCCTGTT
     GTTGTGCCCT ATTATGGCGC GGTGTATCGT CTTGAAATTT TCACGAGTAG TAACCTTTTG CAAGAAGCCC CGCTTTTGAG AGTTCCTAGA ATGGCGACAA hgiAI/aspHI
                      bsp1286
                      bsiHKAI
                      bmyI
                      apaLI/snoI
     bstYI/xhoII      alw44I/snoI   eco57I                                                                  bsrBI
                                                                                                            rcaI
                                                                                                            bspHI
3921 GAGATCCAGT TCGATGTAAC CCACTCGTGC ACCCAACTGA TCTTCAGCAT CTTTTACTTT CACCAGCGTT TCTGGGTGAG CAAAAACAGG AAGGCAAAAT
     CTCTAGGTCA AGCTACATTG GGTGAGCACG TGGGTTGACT AGAAGTCGTA GAAAATGAAA AGTGGTCGCAA AGACCCACTC GTTTTTGTCC TTCCGTTTTA earI/ksp632I    sspI                   hinlI/acyI
                                                                                                                       ahaII/bsaHI        rcaI
                                                                                                                                 aatII   bspHI
4021 GCCGCAAAAA AGGGAATAAG GCCGACACGG AAATGTTGAA TACTCATACT CTTCCTTTTT CAATATTATT GAAGCATTTA TCAGGGTTAT TGTCTCATGA
     CGGCGTTTTT TCCCTTATTC CGGCTGTGCC TTTACAACTT ATGAGTATGA GAAGGAAAAA GTTATAATAA CTTCGTAAAT AGTCCCAATA ACAGAGTACT bspHI
4121 GCGGATACAT ATTTGAATGT ATTTAGAAAA ATAAACAAAT AGGGGTTCCG CGCACATTTC CCCGAAAAGT GCCACCTGAC GTCTAAGAAA CCATTATTAT
     CGCCTATGTA TAAACTTACA TAAATCTTTT TATTTGTTTA TCCCCAAGGC GCGTGTAAAG GGGCTTTTCA CGGTGGACTG CAGATTCTTT GGTAATAATA bpuAI               aseI/asnI/vspI
                               bbsI             xmnI                                                                    psp1406I
                     ecoO109I/draI              asp700    aflII/bfrI                             ahaIII/draI
4221 CATGACATTA ACCTATAAAA ATAGGCGTAT CACGAGGCCC TTTCGTCTTC AAGAATTAAT TCCTTAAGGA ACGTACAGAC GGCTTAAAAG CCTTTAAAAA
     GTACTGTAAT TGGATATTTT TATCCGCATA GTGCTCCGGG AAAGCAGAAG TTCTTAATTA AGGAATTCCT TGCATGTCTG CCGAATTTTC GGAAATTTTT
```

FIG. 6H

```
                                                                                          apoI
                accI                                                                      xmnI
                                                                                          asp700
4321 CGTTTTTAAG GGGTTTGTAG ACAAGGTAAA GGATAAAACA GCACAATTCC AAGAAAAACA CGATTTAGAA CCTAAAAAGA ACGAATTTGA ACTAACTCAT
     GCAAAAATTC CCCAAACATC TGTTCCATTT CCTATTTTGT CGTGTTAAGG TTCTTTTTGT GCTAAATCTT GGATTTTTCT TGCTTAAACT TGATTGAGTA 4421 AACCGAGAGG TAAAAAAAGA ACGAAGTCGA GATCAGGGAA TGAGTTTATA AAATAAAAAA AGCACCTGAA AAGTGTCTT TTTTGATGG TTTTGAACTT
     TTGGCTCTCC ATTTTTTTCT TGCTTCAGCT CTAGTCCCTT ACTCAAATAT TTTATTTTTT TCGTGGACTT TTCCACAGAA AAAAACTACC AAAACTTGAA ahaIII/draI
4521 GTTCTTTCTT ATCTTGATAC ATATAGAAAT AACGTCATTT TTATTTTAGT TGCTGAAAGG TGCGTTGAAG TGTTGGTATG TATGTGTTTT AAAGTATTGA
     CAAGAAAGAA TAGAACTATG TATATCTTTA TTGCAGTAAA AATAAAATCA ACGACTTTCC ACGCAACTTC ACAACCATAC ATACACAAAA TTTCATAACT sspI
4621 AAACCCTTAA AATTGGTTGC ACAGAAAAAC CCCATCTGTT AAAGTTATAA GTGACTAAAC AAATAACTAA ATAGATGGGG GTTTCTTTTA ATATTATGTG
     TTTGGGAATT TTAACCAACG TGTCTTTTTG GGGTAGACAA TTTCAATATT CACTGATTTG TTTATTGATT TATCTACCCC CAAAGAAAAT TATAATACAC styI
                                                                                 ncoI
                                                                                 bsaI dsaI
4721 TCCTAATAGT AGCATTTATT CAGATGAAAA ATCAAGGGTT TTAGTGGACA AGACAAAAAG TGGAAAAGTG AGACCATGGA GAGAAAAGAA AATCGCTAAT
     AGGATTATCA TCGTAAATAA GTCTACTTTT TAGTTCCCAA AATCACCTGT TCTGTTTTTC ACCTTTTCAC TCTGGTACCT CTCTTTTCTT TTAGCGATTA ahaIII/draI
          apoI                                                                                       sspI
4821 GTTGATTACT TTGAACTTCT GCATATTCTT GAATTAAAA AGGCTGAAAG AGTAAAGAT TGTGCTGAAA TATTAGAGTA TAAACAAAAT CGTGAAACAG
     CAACTAATGA AACTTGAAGA CGTATAAGAA CTTAAATTTT TCCGACTTTC TCATTTTCTA ACACGACTTT ATAATCTCAT ATTTGTTTTA GCACTTTGTC xcmI                          gsuI/bpmI                                           bsmI
4921 GCGAAAGAAA GTTGTATCGA GTGTGGTTTT GTAAATCCAG GCTTTGTCCA ATGTGCAACT GGAGGAGAGC AATGAAACAT GGCATTCAGT CACAAAAGGT
     CGCTTTCTTT CAACATAGCT CACACCAAAA CATTTAGGTC CGAAACAGGT TACACGTTGA CCTCCTCTCG TTACTTTGTA CCGTAAGTCA GTGTTTTCCA
```

FIG. 6I

```
                 eco57I                            xcmI
      5021 TGTTGCTGAA GTTATTAAAC AAAAGCCAAC AGTTCGTTGG TTGTTTCTCA CATTAACAGT TAAAAATGTT TATGATGGCG AAGAATTAAA TAAGAGTTTG
           ACAACGACTT CAATAATTTG TTTTCGGTTG TCAAGCAACC AACAAAGAGT GTAATTGTCA ATTTTTACAA ATACTACCGC TTCTTAATTT ATTCTCAAAC aseI/asnI/vspI
      5121 TCAGATATGG CTCAAGGATT TCGCCGAATG ATGCAATATA AAAAATTAA TAAAATCTT GTTGGTTTTA TGCCGTGCAAC GGAAGTGACA ATAAATAATA
           AGTCTATACC GAGTTCCTAA AGCGGCTTAC TACGTTATAT TTTTTTAATT ATTTTTAGAA CAACCAAAAT ACGCACGTTG CCTTCACTGT TATTATTAT nspI
                                          nspHI
                                          ppu10I
                                          nsiI/avaIII
                                          nspI
                                          nspHI                                                      bsaAI
      5221 AAGATAATTC TTATAATCAG CACATGCATG TATTGGTATG TGTGGAACCA ACTTATTTTA AGAATACAGA AATCAAAAAC AATGGATTCA
           TTCTATTAAG AATATTAGTC GTGTACGTAC ATAACCATAC ACACCTTGGT TGAATAAAAT TCTTATGTCT TTAGTTTTTG TTACCTAAGT mcrI                                              munI
      5321 ATTTTGGAAA AAGGCAATGA AATTAGACTA TGATCCAAAT GTAAAAGTTC ACCGAAAAAT AAATATAAAT CGGATATACA ATCGGCAATT
           TAAAACCTTT TTCCGTTACT TTAATCTGAT ACTAGGTTTA CATTTTCAAG TGGCTTTTTA TTTATATTTA GCCTATATGT TAGCCGTTAA apoI      psp1406I
      5421 GACGAAACTG CAAAATATCC TGTAAAGGAT ACGGATTTTA TTAAACCTTG ATGACACAGA AGAAGGCGAT TTGATTCATA CAGATGATGA GGTTTACACC
           CTGCTTTGAC GTTTTATAGG ACATTTCCTA TGCCTAAAAT AATTTGGAAC TACTGTGTCT TCTTCCGCTA AACTAAGTAT GTCTACTACT CCAAATGTGG 5521 GTAAAGGTT AATCTCCTAT GGTGGTTTGT TAAAAGAAAT ACATAAAAAA TTAAACCTTG ATGACACAGA AGAAGGCGAT TTGATTCATA CAGATGATGA
           CATTTCCAA TTAGAGGATA CCACCAAACA ATTTTCTTTA TGTATTTTTT AATTTGGAAC TACTGTGTCT TCTTCCGCTA AACTAAGTAT GTCTACTACT 5621 CGAAAAAGCC GATGAAGATG GATTTTCTAT TATTGCAATG TGGAATTGGG AACGGAAAAA TTATTTTATT AAAGAGTAGT TCAACAAACG GGCCAGTTTG
           GCTTTTTCGG CTACTTCTAC CTAAAAGATA ATAACGTTAC ACCTTAACCC TTGCCTTTTT AATAAAATAA TTTCTCATCA AGTTGTTTGC CCGGTCAAAC
```

FIG. 6J

```
                                                         hgiAI/aspHI
                                                         bsp1286
                                                         bsiHKAI
                          bpuAI                          bmyI         sspI
                          bbsI     aseI/asnI/vspI
5721 TTGAAGATTA GATGCTATAA TTGTTATTAA AAGGATTCTTAG GAAGACGAGT TATTAATAGC TGAATAAGAA CGGTGCTCTC CAAATATTCT
     AACTTCTAAT CTACGATATT AACAATAATT TTCCTAACTT CCTTCTGCTCA ATAATTATCG ACTTATTCTT GCCACGAGAG GTTTATAAGA rcaI
                                                                                                bspHI
5821 TATTTAGAAAA AGCAAATCTA AAATTATCTG AAAAGGGAAT GAGAATAGTG AATGGACCAA TAATAATGAC TAGAGAAGAA TTGTTCATGA
     ATAAATCTTT TCGTTTAGAT TTTAATAGAC TTTTCCCTTA CTCTTATCAC TTACCTGGTT ATTATTACTG ATCTCTTCTT AACAAGTACT hgiJII
                                                                           eco0109I/draII
                                                                           bsp1286
                                                                           bsp120I
                                                                           bmyI
                                                                           banII
                                                                           apaI
5921 AATTAAGGAA CGAATATTGG ATAAATATGG GGATGATGTT AAGGCTATTG GTGTTTATGG CTCTCTTGGT CGTCAGACTG ATGGGCCCTA TTCGGATATT
     TTAATTCCTT GCTTATAACC TATTTATACC CCTACTACAA TTCCGATAAC CACAAATACC GAGAGAACCA GCAGTCTGAC TACCCGGGAT AAGCCTATAA cfr10I                                                              xmnI
                           bsaWI                                                               earI/ksp632I
                           ageI                                                    apoI        asp700
6021 GAGATGATGT GTGTCATGTC AACAGAGGAA GCAGAGTTCA GCCATGAATG GACAACCGGT GAGTGGAAGG TGGAAGTGAA TTTTGATAGC GAAGAGATTC
     CTCTACTACA CACAGTACAG TTGTCTCCTT CGTCTCAAGT CGGTACTTAC CTGTTGGCCA CTCACCTTCC ACCTTCACTT AAAACTATCG CTTCTCTAAG ppu10I           eaeI
        nsiI/avaIII      cfrI
6121 TACTAGATTA TGCATCTCAG GTGGAATCAG ATTGGCCGCT TACACATGGT CAATTTTTCT CTATTTTGCC GATTATGAT TCAGGTGGAT ACTTAGAGAA
     ATGATCTAAT ACGTAGAGTC CACCTTAGTC TAACCGGCGA ATGTGTACCA GTTAAAAAGA GATAAAACGG CTAAATACTA AGTCCACCTA TGAATCTCTT
```

FIG. 6K

```
                                              bsp1286           sapI
                            psp1406I            bmyI          earI/ksp6321
6221 AGTGTATCAA ACTGCTAAAT CGGTAGAAGC CCAAACGTTC CACGATGCGA TTTGTGCCCT TATCGTAGAA GAGCTGTTTG AATATGCAGG CAAATGGCGT
     TCACATAGTT TGACGATTTA GCCATCTTCG GGTTTGCAAG GTGCTACGCT AAACACGGGA ATAGCATCTT CTCGACAAAC TTATACGTCC GTTTACCGCA hglCI
                                                                                      banI             hincII/hindII
     sspI                                        bsp1407I                             bspMI
6321 AATATTCGTG TGCAAGGACC GACAACATTT CTACCATCCT TGACTGTACA GGTAGCAATG GCAGGTGCCA TGTTGATTGG TCTGCATCAT CGCATCTGTT
     TTATAAGCAC ACGTTCCTGG CTGTTGTAAA GATGGTAGGA ACTGACATGT CCATCGTTAC CGTCCACGGT ACAACTAACC AGACGTAGTA GCGTAGACAA haeII                           bstYI/xhoI
          eco47III           eco57I       bglII     eco57I
6421 ATACGACGAG CGCTTCGGTC TTAACTGAAG CAGTTAAGCA ATCAGATCTT CCTTCAGGTT GGAAGTCCAA TACTGGTAGA CACGGTCAAG CATTACAGAC
     TATGCTGCTC GCGAAGCCAG AATTGACTTC GTCAATTCGT TAGTCTAGAA GGAAGTCCAA CCTTCAGGTT ATGACCATCT GTGCCAGTTC GTAATGTCTG apoI
6521 CGACTCTGAG AAACTTCTGG GAATTTCTCG AATCGCTAGA AGGAGTGGAC AGAACGACAC GGATATATAG TGGATGTGTC AAAACGCATA
     GCTGAGACTC TTTGAAGACC CTTAAAGAGC TTAGCGATCT TCCTCACCTG TCTTGCTGTG CCTATATATC ACCTACACAG TTTTGCGTAT snaBI
                bsaAI                                                asnI/vspI
6621 CCATTTTGAA CGATGACCTC TAATAATTGT GGTTACGTAT TTATTAACTT CTCCTAGTAT TAGTAATTAT CATGGCTGTC ATGGCGCATT
     GGTAAAACTT GCTACTGGAG ATTATTAACA CCAATGCATA AATAATTGAA GAGGATCATA ATCATTAATA GTACCGACAG TACCGCGTAA aseI/vspI                     aseI/asnI/vspI
6721 AACGGAATAA AGGGTGTGCT TAAATCGGGC CATTTTTGCGT AATAAGAAAA AGGATTAATT ATGAGCGAAT TGAATTAATA ATAAGGTAAT AGATTTACAT
     TTGCCTTATT TCCCACACGA ATTTAGCCCG GTAAAAACGCA TTATTCTTTT TCCTAATTAA TACTCGCTTA ACTTAATTAT TATTCCATTA TCTAAATGTA 6821 TAGAAAATGA AAGGGGATTT TATGCGTGAG AATGTTACAG TCTATCCCGG CAATAGTTAC CCTTATTATC AAGATAAGAA AGAAAAGGAT TTTTCGCTAC
     ATCTTTTACT TTCCCCTAAA ATACGCACTC TTACAATGTC AGATAGGGCC GTTATCAATG GGAATAATAG TTCTATTCTT TCTTTTCCTA AAAAGCGATG
```

FIG. 6L

```
                  ahaIII/draI
6921  GCTCAAATCC TTTAAAAAAA CACAAAAGAC CACATTTTTT AATGTGGTCT TTATTCTTCA ACTAAAGCAC CCATTAGTTC AACAAACGAA AATTGGATAA
      CGAGTTTAGG AAATTTTTTT GTGTTTTCTG GTGTAAAAAA TTACACCAGA AATAAGAAGT TGATTTCCGTG GGTAATCAAG TTGTTTGCTT TTAACCTATT
                    ahaIII/draI          sspI                                                                  apoI
7021  AGTGGGATAT TTTTAAAATA TATATTTTATG TTACAGTAAT ATTGACTTTT AAAAAAGGAT TGATTCTAAT GAAGAAAGCA GACAAGTAAG CCTCCTAAAT
      TCACCCTATA AAAATTTTAT ATATAAAATAC AATGTCATTA TAACTGAAAA TTTTTTCCTA ACTAAGATTA CTTCTTTCGT CTGTTCATTC GGAGGATTTA
              apoI                                                    munI    earI/ksp632I
7121  TCACTTTTAGA TAAAATTTA GGAGGCATAT CAAATGAACT TTAATAAAAT TGATTTAGAC AATTGGAAGA GAAAAGAGAT ATTTAATCAT TATTTGAACC
      AGTGAAATCT ATTTTTAAAT CCTCCGTATA GTTTACTTGA AATTATTTTA ACTAAATCTG TTAACCTTCT CTTTTCTCTA TAAATTAGTA ATAAACTTGG
                                                                                                  apoI
7221  AACAAACGAC TTTTTAGTATA ACCACAGAAA TTGATATTAG TGTTTTATAC CGAAACATAA AACAAGAAGG ATATAAATTT TACCCTGCAT TTATTTTCTT
      TTGTTTGCTG AAAATCATAT TGGTGTCTTT AACTATAATC ACAAAATATG GCTTTGTATT TTGTTCTTCC TATATTTAAA ATGGGACGTA AATAAAAGAA 7321  AGTGACAAGG GTGATAAACT CAAATACAGC TTTTAGAACT GGTTACAATA GCGACGGAGA GTTAGGTTAT TGGGATAAGT TAGAGCCACT TTATACAATT
      TCACTGTTCC CACTATTTGA GTTTATGTCG AAAATCTTGA CCAATGTTAT CGCTGCCTCT CAATCCAATA ACCCTATTCA ATCTCGGTGA AATATGTTAA
                                                              xmnI
                                                              asp700                                    styI
                                                                                                        ncoI
                                                                                                        dsaI
7421  TTTGATGGTG TATCTAAAAC ATTCTCTGGT ATTGGACTTC CTGTAAAGAA TGACTTCAAA GAGTTTTATG ATTTATACCT TTCTGATGTA GAGAAATATA
      AAACTACCAC ATAGATTTTG TAAGAGACCA TAACCTGAAG GACATTTCTT ACTGAAGTTT CTCAAAATAC TAAATATGGA AAGACTACAT CTCTTTATAT apoI asel/asnI/vspI
7521  ATGGTTCGGG GAAATTGTTT CCCAAAACAC CTATACCTGA AAATGCTTTT TCTCTTTCTA TTATTCCATG GACTTCATTT ACTGGGTTTA ACTTAAATAT
      TACCAAGCCC CTTTAACAAA GGGTTTTGTG GATATGGACT TTTACGAAAA AGAGAAAGAT AATAAGGTAC CTGAAGTAAA TGACCCAAAT TGAATTTATA 7621  CAATAATAAT AGTAATTACC TTCTACCCAT TATTACAGCA GGAAAATTCA TTAATAAAGG TAATTCAATA TATCTTTACA GGTACATCAT
      GTTATTATTA TCATTAATGG AAGATGGGTA ATAATGTCGT CCTTTTAAGT AATTATTTCC ATTAAGTTAT ATAAATGGCG ATAGAAATGT CCATGTAGTA
```

FIG. 6M

```
            mamI                                      stuI
            bsaBI                                     haeI
7721 TCTGTTTGTG ATGGTTATCA TGCAGGATTG TTTATGAACT CTATTCAGGA ATTGTCAGAT AGGCCTAATG ACTGGCTTTT ATAATATGAG ATAATGCCGA
     AGACAAACAC TACCAATAGT ACGTCCTAAC AAATACTTGA GATAAGTCCT TAACAGTCTA TCCGGATTAC TGACCGAAAA TATTATACTC TATTACGGCT mamI[dam-]
                                                                                 bsaBI[dam-]
                                 bspMI                                           bstYI/xhoII
                                                                                 gsuI/bpmI
7821 CTGTACTTTT TACAGTCGGT TTTCTAATGT CACTAACCTG CCCCGTTAGT TGAAGAAGGT TTTTATATTA CAGCTCCAGA TCCATATCCT TCTTTTTCTG
     GACATGAAAA ATGTCAGCCA AAAGATTACA GTGATTGGAC GGGGCAATCA ACTTCTTCCA AAAATATAAT GTCGAGGTCT AGGTATAGGA AGAAAAAGAC munI
7921 AACCGACTTC TCCTTTTTCG CTTCTTTATT CCAATTGCTT TATTGACGTT GAGCCTCGGA ACCCXTATAG TGTGTTATAC TTTACTTGGA AGTGGTTGCC
     TTGGCTGAAG AGGAAAAAGC GAAGAAATAA GGTTAACGAA ATAACTGCAA CTCGGAGCCT TGGG?ATATC ACACAATATG AAATGAACCT TCACCAACGG ndeI                                                             bsmI
8021 GGAAAGAGCG AAAATGCCTC ACATTTGTGC CACCTAAAAA GGAGCCGATTT ACATATGAGT TATGCAGTTT GTAGAATGCA AAAAGTGAAA TCAGGATCX
     CCTTTCTCGC TTTTACGGAG TGTAAACACG GTGGATTTTT CCTCGGCTAAA TGTATACTCA ATACGTCAAA CATCTTACGT TTTTCACTTT AGTCCTAG?
```

FIG. 6N

SEQUENCE LISTING ( 1 ) GENERAL INFORMATION:

( i i i ) NUMBER OF SEQUENCES: 74

( 2 ) INFORMATION FOR SEQ ID NO:1:

( i ) SEQUENCE CHARACTERISTICS:
      ( A ) LENGTH: 8119 base pairs
      ( B ) TYPE: Nucleic Acid
      ( C ) STRANDEDNESS: Single
      ( D ) TOPOLOGY: Linear ( x i ) SEQUENCE DESCRIPTION: SEQ ID NO:1:

```
GAATTCNGGT  CTACTAAAAT  ATTATTCCAT  ACTATACAAT  TAATACACAG                    50

AATAATCTGT  CTATTGGTTA  TTCTGCAAAT  GAAAAAAAGG  AGAGGATAAA                   100

GA    GTG  AGA  GGC  AAA  AAA  GTA  TGG  ATC  AGT  TTG  CTG  TTT            138
      Val  Arg  Gly  Lys  Lys  Val  Trp  Ile  Ser  Leu  Leu  Phe
      -107      -105                 -100

GCT  TTA  GCG  TTA  ATC  TTT  ACG  ATG  GCG  TTC  GGC  AGC  ACA             177
Ala  Leu  Ala  Leu  Ile  Phe  Thr  Met  Ala  Phe  Gly  Ser  Thr
-95                      -90                      -85

TCC  TCT  GCC  CAG  GCG  GCA  GGG  AAA  TCA  AAC  GGG  GAA  AAG             216
Ser  Ser  Ala  Gln  Ala  Ala  Gly  Lys  Ser  Asn  Gly  Glu  Lys
          -80                 -75                      -70

AAA  TAT  ATT  GTC  GGG  TTT  AAA  CAG  ACA  ATG  AGC  ACG  ATG             255
```

-continued

| | |
|---|---|
| Lys Tyr Ile Val Gly Phe Lys Gln Thr Met Ser Thr Met<br>-65                    -60 | |
| AGC GCC GCT AAG AAG AAA GAT GTC ATT TCT GAA AAA GGC<br>Ser Ala Ala Lys Lys Lys Asp Val Ile Ser Glu Lys Gly<br>    -55              -50                  -45 | 294 |
| GGG AAA GTG CAA AAG CAA TTC AAA TAT GTA GAC GCA GCT<br>Gly Lys Val Gln Lys Gln Phe Lys Tyr Val Asp Ala Ala<br>        -40              -35 | 333 |
| TCA GCT ACA TTA AAC GAA AAA GCT GTA AAA GAA TTG AAA<br>Ser Ala Thr Leu Asn Glu Lys Ala Val Lys Glu Leu Lys<br>-30              -25              -20 | 372 |
| AAA GAC CCG AGC GTC GCT TAC GTT GAA GAA GAT CAC GTA<br>Lys Asp Pro Ser Val Ala Tyr Val Glu Glu Asp His Val<br>        -15              -10                  -5 | 411 |
| GCA CAT GCG TAC GCG CAG TCC GTG CCT TAC GGC GTA TCA<br>Ala His Ala Tyr Ala Gln Ser Val Pro Tyr Gly Val Ser<br>                1                5 | 450 |
| CAA ATT AAA GCC CCT GCT CTG CAC TCT CAA GGC TAC ACT<br>Gln Ile Lys Ala Pro Ala Leu His Ser Gln Gly Tyr Thr<br>10              15              20 | 489 |
| GGA TCA AAT GTT AAA GTA GCG GTT ATC GAC AGC GGT ATC<br>Gly Ser Asn Val Lys Val Ala Val Ile Asp Ser Gly Ile<br>    25              30                  35 | 528 |
| GAT TCT TCT CAT CCT GAT TTA AAG GTA GCA GGC GGA GCC<br>Asp Ser Ser His Pro Asp Leu Lys Val Ala Gly Gly Ala<br>                40              45 | 567 |
| AGC ATG GTT CCT TCT GAA ACA AAT CCT TTC CAA GAC AAC<br>Ser Met Val Pro Ser Glu Thr Asn Pro Phe Gln Asp Asn<br>    50              55              60 | 606 |
| GAC TCT CAC GGA ACT CAC GTT GCC GGC ACA GTT GCG GCT<br>Asp Ser His Gly Thr His Val Ala Gly Thr Val Ala Ala<br>            65              70 | 645 |
| CTT AAT AAC TCA ATC GGT GTA TTA GGC GTT GCG CCA AGC<br>Leu Asn Asn Ser Ile Gly Val Leu Gly Val Ala Pro Ser<br>75              80              85 | 684 |
| GCA TCA CTT TAC GCT GTA AAA GTT CTC GGT GCT GAC GGT<br>Ala Ser Leu Tyr Ala Val Lys Val Leu Gly Ala Asp Gly<br>        90              95                  100 | 723 |
| TCC GGC CAA TAC AGC TGG ATC ATT AAC GGA ATC GAG TGG<br>Ser Gly Gln Tyr Ser Trp Ile Ile Asn Gly Ile Glu Trp<br>            105              110 | 762 |
| GCG ATC GCA AAC AAT ATG GAC GTT ATT AAC ATG AGC CTC<br>Ala Ile Ala Asn Asn Met Asp Val Ile Asn Met Ser Leu<br>115              120              125 | 801 |
| GGC GGA CCT TCT GGT TCT GCT GCT TTA AAA GCG GCA GTT<br>Gly Gly Pro Ser Gly Ser Ala Ala Leu Lys Ala Ala Val<br>        130              135 | 840 |
| GAT AAA GCC GTT GCA TCC GGC GTC GTA GTC GTT GCG GCA<br>Asp Lys Ala Val Ala Ser Gly Val Val Val Val Ala Ala<br>140              145              150 | 879 |
| GCC GGT AAC GAA GGC ACT TCC GGC AGC TCG TCG ACA GTG<br>Ala Gly Asn Glu Gly Thr Ser Gly Ser Ser Ser Thr Val<br>        155              160                  165 | 918 |
| GAC TAC CCT GGC AAA TAC CCT TCT GTC ATT GCA GTA GGC<br>Asp Tyr Pro Gly Lys Tyr Pro Ser Val Ile Ala Val Gly<br>                170              175 | 957 |
| GCT GTT GAC AGC AGC AAC CAA AGA GCA TCT TTC TCA AGC<br>Ala Val Asp Ser Ser Asn Gln Arg Ala Ser Phe Ser Ser<br>180              185              190 | 996 |
| GTA GGA CCT GAG CTT GAT GTC ATG GCA CCT GGC GTA TCT | 1035 |

```
Val Gly Pro Glu Leu Asp Val Met Ala Pro Gly Val Ser
            195                 200

ATC CAA AGC ACG CTT CCT GGA AAC AAA TAC GGG GCG TAC              1074
Ile Gln Ser Thr Leu Pro Gly Asn Lys Tyr Gly Ala Tyr
205                 210                 215

AAC GGT ACC TCA ATG GCA TCT CCG CAC GTT GCC GGA GCG              1113
Asn Gly Thr Ser Met Ala Ser Pro His Val Ala Gly Ala
        220                 225                 230

GCT GCT TTG ATT CTT TCT AAG CAC CCG AAC TGG ACA AAC              1152
Ala Ala Leu Ile Leu Ser Lys His Pro Asn Trp Thr Asn
                235                 240

ACT CAA GTC CGC AGC AGT TTA GAA AAC ACC ACT ACA AAA              1191
Thr Gln Val Arg Ser Ser Leu Glu Asn Thr Thr Thr Lys
        245                 250                 255

CTT GGT GAT TCT TTC TAC TAT GGA AAA GGG CTG ATC AAC              1230
Leu Gly Asp Ser Phe Tyr Tyr Gly Lys Gly Leu Ile Asn
                260                 265

GTA CAG GCG GCA GCT CAG TA AAACATAAAA AACCGGCCTT                 1270
Val Gln Ala Ala Ala Gln
270                 275

GGCCCCGCCG GTTTTTATT  ATTTTTCTTC  CTCCGCATGT  TCAATCCGCT         1320

CCATAATCGA CGGATGGCTC CCTCTGAAAA TTTTAACGAG AAACGGCGGG           1370

TTGACCCGGC TCAGTCCCGT AACGGCAAG  TCCTGAAACG  TCTCAATCGC          1420

CGCTTCCCGG TTTCCGGTCA GCTCAATGCC GTAACGGTCG GCGGCGTTTT          1470

CCTGATACCG GGAGACGGCA TTCGTAATCG GATCCGGAAA TTGTAAACGT          1520

TAATATTTTG TTAAAATTCG CGTTAAATTT TTGTTAAATC AGCTCATTTT         1570

TTAACCAATA GGCCGAAATC GGCAAAATCC CTTATAAATC AAAAGAATAG         1620

ACCGAGATAG GGTTGAGTGT TGTTCCAGTT TGGAACAAGA GTCCACTATT         1670

AAAGAACGTG GACTCCAACG TCAAAGGGCG AAAAACCGTC TATCAGGGCT         1720

ATGGCCCACT ACGTGAACCA TCACCCTAAT CAAGTTTTTT GGGGTCGAGG         1770

TGCCGTAAAG CACTAAATCG GAACCCTAAA GGGAGCCCCC GATTTAGAGC         1820

TTGACGGGGA AAGCCGGCGA ACGTGGCGAG AAAGGAAGGG AAGAAAGCGA         1870

AAGGAGCGGG CGCTAGGGCG CTGGCAAGTG TAGCGGTCAC GCTGCGCGTA         1920

ACCACCACAC CCGCCGCGCT TAATGCGCCG CTACAGGGCG CGTCCGGATC         1970

NGATCCGACG CGAGGCTGGA TGGCCTTCCC CATTATGATT CTTCTCGCTT         2020

CCGGCGGCAT CGGGATGCCC GCGTTGCAGG CCATGCTGTC CAGGCAGGTA         2070

GATGACGACC ATCAGGGACA GCTTCAAGGA TCGCTCGCGG CTCTTACCAG         2120

CCTAACTTCG ATCACTGGAC CGCTGATCGT CACGGCGATT TATGCCGCCT         2170

CGGCGAGCAC ATGGAACGGG TTGGCATGGA TTGTAGGCGC CGCCCTATAC         2220

CTTGTCTGCC TCCCCGCGTT GCGTCGCGGT GCATGGAGCC GGGCCACCTC         2270

GACCTGAATG GAAGCCGGCG GCACCTCGCT AACGGATTCA CCACTCCAAG         2320

AATTGGAGCC AATCAATTCT TGCGGAGAAC TGTGAATGCG CAAACCAACC         2370

CTTGGCAGAA CATATCCATC GCGTCCGCCA TCTCCAGCAG CCGCACGCGG         2420

CGCATCTCGG GCCGCGTTGC TGGCGTTTTT CCATAGGCTC CGCCCCCCTG         2470

ACGAGCATCA CAAAAATCGA CGCTCAAGTC AGAGGTGGCG AAACCCGACA         2520

GGACTATAAA GATACCAGGC GTTTCCCCCT GGAAGCTCCC TCGTGCGCTC         2570

TCCTGTTCCG ACCCTGCCGC TTACCGGATA CCTGTCCGCC TTTCTCCCTT         2620
```

```
CGGGAAGCGT GGCGCTTTCT CAATGCTCAC GCTGTAGGTA TCTCAGTTCG      2670
GTGTAGGTCG TTCGCTCCAA GCTGGGCTGT GTGCACGAAC CCCCCGTTCA      2720
GCCCGACCGC TGCGCCTTAT CCGGTAACTA TCGTCTTGAG TCCAACCCGG      2770
TAAGACACGA CTTATCGCCA CTGGCAGCAG CCACTGGTAA CAGGATTAGC      2820
AGAGCGAGGT ATGTAGGCGG TGCTACAGAG TTCTTGAAGT GGTGGCCTAA      2870
CTACGGCTAC ACTAGAAGGA CAGTATTTGG TATCTGCGCT CTGCTGAAGC      2920
CAGTTACCTT CGGAAAAAGA GTTGGTAGCT CTTGATCCGG CAAACAAACC      2970
ACCGCTGGTA GCGGTGGTTT TTTTGTTTGC AAGCAGCAGA TTACGCGCAG      3020
AAAAAAGGA TCTCAAGAAG ATCCTTTGAT CTTTTCTACG GGGTCTGACG       3070
CTCAGTGGAA CGAAAACTCA CGTTAAGGGA TTTTGGTCAT GAGATTATCA     3120
AAAAGGATCT TCACCTAGAT CCTTTTAAAT TAAAAATGAA GTTTTAAATC     3170
AATCTAAAGT ATATATGAGT AAACTTGGTC TGACAGTTAC CAATGCTTAA     3220
TCAGTGAGGC ACCTATCTCA GCGATCTGTC TATTTCGTTC ATCCATAGTT    3270
GCCTGACTCC CCGTCGTGTA GATAACTACG ATACGGGAGG GCTTACCATC    3320
TGGCCCCAGT GCTGCAATGA TACCGCGAGA CCCACGCTCA CCGGCTCCAG    3370
ATTTATCAGC AATAAACCAG CCAGCCGGAA GGGCCGAGCG CAGAAGTGGT    3420
CCTGCAACTT TATCCGCCTC CATCCAGTCT ATTAATTGTT GCCGGGAAGC    3470
TAGAGTAAGT AGTTCGCCAG TTAATAGTTT GCGCAACGTT GTTGCCATTG    3520
CTGCAGGCAT CGTGGTGTCA CGCTCGTCGT TTGGTATGGC TTCATTCAGC    3570
TCCGGTTCCC AACGATCAAG GCGAGTTACA TGATCCCCCA TGTTGTGCAA    3620
AAAAGCGGTT AGCTCCTTCG GTCCTCCGAT CGTTGTCAGA AGTAAGTTGG    3670
CCGCAGTGTT ATCACTCATG GTTATGGCAG CACTGCATAA TTCTCTTACT    3720
GTCATGCCAT CCGTAAGATG CTTTTCTGTG ACTGGTGAGT ACTCAACCAA    3770
GTCATTCTGA GAATAGTGTA TGCGGCGACC GAGTTGCTCT TGCCCGGCGT    3820
CAACACGGGA TAATACCGCG CCACATAGCA GAACTTTAAA AGTGCTCATC    3870
ATTGGAAAAC GTTCTTCGGG GCGAAAACTC TCAAGGATCT TACCGCTGTT    3920
GAGATCCAGT TCGATGTAAC CCACTCGTGC ACCCAACTGA TCTTCAGCAT    3970
CTTTTACTTT CACCAGCGTT TCTGGGTGAG CAAAAACAGG AAGGCAAAAT    4020
GCCGCAAAAA AGGGAATAAG GGCGACACGG AAATGTTGAA TACTCATACT    4070
CTTCCTTTTT CAATATTATT GAAGCATTTA TCAGGGTTAT TGTCTCATGA    4120
GCGGATACAT ATTTGAATGT ATTTAGAAAA ATAAACAAAT AGGGGTTCCG    4170
CGCACATTTC CCCGAAAAGT GCCACCTGAC GTCTAAGAAA CCATTATTAT    4220
CATGACATTA ACCTATAAAA ATAGGCGTAT CACGAGGCCC TTTCGTCTTC    4270
AAGAATTAAT TCCTTAAGGA ACGTACAGAC GGCTTAAAAG CCTTTAAAAA    4320
CGTTTTTAAG GGGTTTGTAG ACAAGGTAAA GGATAAAACA GCACAATTCC    4370
AAGAAAAACA CGATTAGAA CCTAAAAGA ACGAATTTGA ACTAACTCAT      4420
AACCGAGAGG TAAAAAAGA ACGAAGTCGA GATCAGGGAA TGAGTTTATA     4470
AAATAAAAAA AGCACCTGAA AAGGTGTCTT TTTTGATGG TTTTGAACTT     4520
GTTCTTTCTT ATCTTGATAC ATATAGAAAT AACGTCATTT TTATTTTAGT    4570
TGCTGAAAGG TGCGTTGAAG TGTTGGTATG TATGTGTTTT AAAGTATTGA   4620
```

```
AAACCCTTAA AATTGGTTGC ACAGAAAAAC CCCATCTGTT AAAGTTATAA         4670
GTGACTAAAC AAATAACTAA ATAGATGGGG GTTTCTTTTA ATATTATGTG         4720
TCCTAATAGT AGCATTTATT CAGATGAAAA ATCAAGGGTT TTAGTGGACA         4770
AGACAAAAAG TGGAAAAGTG AGACCATGGA GAGAAAGAA AATCGCTAAT          4820
GTTGATTACT TTGAACTTCT GCATATTCTT GAATTAAAA AGGCTGAAAG          4870
AGTAAAAGAT TGTGCTGAAA TATTAGAGTA TAAACAAAAT CGTGAAACAG         4920
GCGAAAGAAA GTTGTATCGA GTGTGGTTTT GTAAATCCAG GCTTTGTCCA         4970
ATGTGCAACT GGAGGAGAGC AATGAAACAT GGCATTCAGT CACAAAAGGT         5020
TGTTGCTGAA GTTATTAAAC AAAAGCCAAC AGTTCGTTGG TTGTTTCTCA         5070
CATTAACAGT TAAAAATGTT TATGATGGCG AAGAATTAAA TAAGAGTTTG         5120
TCAGATATGG CTCAAGGATT TCGCCGAATG ATGCAATATA AAAAAATTAA         5170
TAAAAATCTT GTTGGTTTTA TGCGTGCAAC GGAAGTGACA ATAAATAATA         5220
AAGATAATTC TTATAATCAG CACATGCATG TATTGGTATG TGTGGAACCA         5270
ACTTATTTTA AGAATACAGA AAACTACGTG AATCAAAAC AATGGATTCA          5320
ATTTTGGAAA AAGGCAATGA AATTAGACTA TGATCCAAAT GTAAAAGTTC         5370
AAATGATTCG ACCGAAAAAT AAATATAAAT CGGATATACA ATCGGCAATT         5420
GACGAAACTG CAAAATATCC TGTAAAGGAT ACGGATTTTA TGACCGATGA         5470
TGAAGAAAAG AATTTGAAAC GTTTGTCTGA TTTGGAGGAA GGTTTACACC         5520
GTAAAGGTT AATCTCCTAT GGTGGTTTGT TAAAAGAAAT ACATAAAAAA          5570
TTAAACCTTG ATGACACAGA AGAAGGCGAT TGATTCATA CAGATGATGA          5620
CGAAAAGCC GATGAAGATG GATTTTCTAT TATTGCAATG TGGAATTGGG          5670
AACGGAAAAA TTATTTTATT AAAGAGTAGT TCAACAAACG GGCCAGTTTG         5720
TTGAAGATTA GATGCTATAA TTGTTATTAA AAGGATTGAA GGATGCTTAG         5770
GAAGACGAGT TATTAATAGC TGAATAAGAA CGGTGCTCTC CAAATATTCT         5820
TATTTAGAAA AGCAAATCTA AAATTATCTG AAAAGGGAAT GAGAATAGTG         5870
AATGGACCAA TAATAATGAC TAGAGAAGAA AGAATGAAGA TTGTTCATGA         5920
AATTAAGGAA CGAATATTGG ATAAATATGG GGATGATGTT AAGGCTATTG         5970
GTGTTTATGG CTCTCTTGGT CGTCAGACTG ATGGGCCCTA TTCGGATATT         6020
GAGATGATGT GTGTCATGTC AACAGAGGAA GCAGAGTTCA GCCATGAATG         6070
GACAACCGGT GAGTGGAAGG TGGAAGTGAA TTTTGATAGC GAAGAGATTC         6120
TACTAGATTA TGCATCTCAG GTGGAATCAG ATTGGCCGCT TACACATGGT         6170
CAATTTTTCT CTATTTTGCC GATTTATGAT TCAGGTGGAT ACTTAGAGAA         6220
AGTGTATCAA ACTGCTAAAT CGGTAGAAGC CCAAACGTTC CACGATGCGA         6270
TTTGTGCCCT TATCGTAGAA GAGCTGTTTG AATATGCAGG CAAATGGCGT         6320
AATATTCGTG TGCAAGGACC GACAACATTT CTACCATCCT TGACTGTACA         6370
GGTAGCAATG GCAGGTGCCA TGTTGATTGG TCTGCATCAT CGCATCTGTT         6420
ATACGACGAG CGCTTCGGTC TTAACTGAAG CAGTTAAGCA ATCAGATCTT         6470
CCTTCAGGTT ATGACCATCT GTGCCAGTTC GTAATGTCTG GTCAACTTTC         6520
CGACTCTGAG AAACTTCTGG AATCGCTAGA GAATTTCTGG AATGGGATTC         6570
AGGAGTGGAC AGAACGACAC GGATATATAG TGGATGTGTC AAAACGCATA         6620
```

```
CCATTTTGAA CGATGACCTC TAATAATTGT TAATCATGTT GGTTACGTAT      6670
TTATTAACTT CTCCTAGTAT TAGTAATTAT CATGGCTGTC ATGGCGCATT      6720
AACGGAATAA AGGGTGTGCT TAAATCGGGC CATTTTGCGT AATAAGAAAA      6770
AGGATTAATT ATGAGCGAAT TGAATTAATA ATAAGGTAAT AGATTTACAT      6820
TAGAAAATGA AAGGGGATTT TATGCGTGAG AATGTTACAG TCTATCCCGG      6870
CAATAGTTAC CCTTATTATC AAGATAAGAA AGAAAAGGAT TTTTCGCTAC      6920
GCTCAAATCC TTTAAAAAAA CACAAAAGAC CACATTTTTT AATGTGGTCT      6970
TTATTCTTCA ACTAAAGCAC CCATTAGTTC AACAAACGAA AATTGGATAA      7020
AGTGGGATAT TTTTAAAATA TATATTTATG TTACAGTAAT ATTGACTTTT      7070
AAAAAAGGAT TGATTCTAAT GAAGAAAGCA GACAAGTAAG CCTCCTAAAT      7120
TCACTTTAGA TAAAAATTTA GGAGGCATAT CAAATGAACT TTAATAAAAT      7170
TGATTTAGAC AATTGGAAGA GAAAGAGAT ATTTAATCAT TATTTGAACC       7220
AACAAACGAC TTTTAGTATA ACCACAGAAA TTGATATTAG TGTTTTATAC      7270
CGAAACATAA AACAAGAAGG ATATAAATTT TACCCTGCAT TTATTTTCTT     7320
AGTGACAAGG GTGATAAACT CAAATACAGC TTTTAGAACT GGTTACAATA      7370
GCGACGGAGA GTTAGGTTAT TGGGATAAGT TAGAGCCACT TTATACAATT      7420
TTTGATGGTG TATCTAAAAC ATTCTCTGGT ATTTGGACTC CTGTAAAGAA      7470
TGACTTCAAA GAGTTTTATG ATTTATACCT TTCTGATGTA GAGAAATATA      7520
ATGGTTCGGG GAAATTGTTT CCCAAAACAC CTATACCTGA AAATGCTTTT      7570
TCTCTTTCTA TTATTCCATG GACTTCATTT ACTGGGTTTA ACTTAAATAT      7620
CAATAATAAT AGTAATTACC TTCTACCCAT TATTACAGCA GGAAAATTCA      7670
TTAATAAAGG TAATTCAATA TATTTACCGC TATCTTTACA GGTACATCAT      7720
TCTGTTTGTG ATGGTTATCA TGCAGGATTG TTTATGAACT CTATTCAGGA      7770
ATTGTCAGAT AGGCCTAATG ACTGGCTTTT ATAATATGAG ATAATGCCGA      7820
CTGTACTTTT TACAGTCGGT TTTCTAATGT CACTAACCTG CCCCGTTAGT      7870
TGAAGAAGGT TTTTATATTA CAGCTCCAGA TCCATATCCT TCTTTTTCTG      7920
AACCGACTTC TCCTTTTTCG CTTCTTTATT CCAATTGCTT TATTGACGTT      7970
GAGCCTCGGA ACCCNTATAG TGTGTTATAC TTTACTTGGA AGTGGTTGCC      8020
GGAAAGAGCG AAAATGCCTC ACATTTGTGC CACCTAAAAA GGAGCGATTT      8070
ACATATGAGT TATGCAGTTT GTAGAATGCA AAAGTGAAA  TCAGGATCN      8119
```

( 2 ) INFORMATION FOR SEQ ID NO:2:

( i ) SEQUENCE CHARACTERISTICS:
( A ) LENGTH: 382 amino acids
( B ) TYPE: Amino Acid
( D ) TOPOLOGY: Linear ( x i ) SEQUENCE DESCRIPTION: SEQ ID NO:2:

```
Val  Arg  Gly  Lys  Lys  Val  Trp  Ile  Ser  Leu  Leu  Phe  Ala  Leu  Ala
-107      -105                -100                     -95

Leu  Ile  Phe  Thr  Met  Ala  Phe  Gly  Ser  Thr  Ser  Ser  Ala  Gln  Ala
          -90                      -85                      -80

Ala  Gly  Lys  Ser  Asn  Gly  Glu  Lys  Lys  Tyr  Ile  Val  Gly  Phe  Lys
          -75                      -70                      -65
```

```
Gln Thr Met Ser Thr Met Ser Ala Ala Lys Lys Lys Asp Val Ile
        -60             -55                 -50
Ser Glu Lys Gly Gly Lys Val Gln Lys Gln Phe Lys Tyr Val Asp
        -45             -40                 -35
Ala Ala Ser Ala Thr Leu Asn Glu Lys Ala Val Lys Glu Leu Lys
        -30             -25                 -20
Lys Asp Pro Ser Val Ala Tyr Val Glu Glu Asp His Val Ala His
        -15             -10                  -5
Ala Tyr Ala Gln Ser Val Pro Tyr Gly Val Ser Gln Ile Lys Ala
             1           5                   10
Pro Ala Leu His Ser Gln Gly Tyr Thr Gly Ser Asn Val Lys Val
            15          20                   25
Ala Val Ile Asp Ser Gly Ile Asp Ser Ser His Pro Asp Leu Lys
            30          35                   40
Val Ala Gly Gly Ala Ser Met Val Pro Ser Glu Thr Asn Pro Phe
            45          50                   55
Gln Asp Asn Asp Ser His Gly Thr His Val Ala Gly Thr Val Ala
            60          65                   70
Ala Leu Asn Asn Ser Ile Gly Val Leu Gly Val Ala Pro Ser Ala
            75          80                   85
Ser Leu Tyr Ala Val Lys Val Leu Gly Ala Asp Gly Ser Gly Gln
            90          95                  100
Tyr Ser Trp Ile Ile Asn Gly Ile Glu Trp Ala Ile Ala Asn Asn
           105         110                  115
Met Asp Val Ile Asn Met Ser Leu Gly Gly Pro Ser Gly Ser Ala
           120         125                  130
Ala Leu Lys Ala Ala Val Asp Lys Ala Val Ala Ser Gly Val Val
           135         140                  145
Val Val Ala Ala Ala Gly Asn Glu Gly Thr Ser Gly Ser Ser Ser
           150         155                  160
Thr Val Asp Tyr Pro Gly Lys Tyr Pro Ser Val Ile Ala Val Gly
           165         170                  175
Ala Val Asp Ser Ser Asn Gln Arg Ala Ser Phe Ser Ser Val Gly
           180         185                  190
Pro Glu Leu Asp Val Met Ala Pro Gly Val Ser Ile Gln Ser Thr
           195         200                  205
Leu Pro Gly Asn Lys Tyr Gly Ala Tyr Asn Gly Thr Ser Met Ala
           210         215                  220
Ser Pro His Val Ala Gly Ala Ala Ala Leu Ile Leu Ser Lys His
           225         230                  235
Pro Asn Trp Thr Asn Thr Gln Val Arg Ser Ser Leu Glu Asn Thr
           240         245                  250
Thr Thr Lys Leu Gly Asp Ser Phe Tyr Tyr Gly Lys Gly Leu Ile
           255         260                  265
Asn Val Gln Ala Ala Ala Gln
           270         275
```

( 2 ) INFORMATION FOR SEQ ID NO:3:

( i ) SEQUENCE CHARACTERISTICS:
      ( A ) LENGTH: 7 amino acids
      ( B ) TYPE: Amino Acid
      ( D ) TOPOLOGY: Linear ( x i ) SEQUENCE DESCRIPTION: SEQ ID NO:3:

Ser Leu Gly Gly Pro Ser Gly (2) INFORMATION FOR SEQ ID NO:4:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO:4:

```
Ala  Ala  Ala  Gly  Asn  Glu  Gly
 1                 5         7
```

(2) INFORMATION FOR SEQ ID NO:5:

(i) SEQUENCE CHARACTERISTICS:
        (A) LENGTH: 6 amino acids
        (B) TYPE: Amino Acid
        (D) TOPOLOGY: Linear (xi) SEQUENCE DESCRIPTION: SEQ ID NO:5:

```
Ser  Thr  Val  Gly  Tyr  Pro
 1                 5    6
```

(2) INFORMATION FOR SEQ ID NO:6:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO:6:

```
Ser  Trp  Gly  Pro  Ala  Asp  Asp
 1                 5         7
```

(2) INFORMATION FOR SEQ ID NO:7:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO:7:

```
Phe  Ala  Ser  Gly  Asn  Gly  Gly
 1                 5         7
```

(2) INFORMATION FOR SEQ ID NO:8:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO:8:

```
Cys  Asn  Tyr  Asp  Gly  Tyr  Thr
 1                 5         7
```

(2) INFORMATION FOR SEQ ID NO:9:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO:9:

```
Ser  Trp  Gly  Pro  Glu  Asp  Asp
 1                 5         7
```

( 2 ) INFORMATION FOR SEQ ID NO:10:

( i ) SEQUENCE CHARACTERISTICS:
            ( A ) LENGTH: 7 amino acids
            ( B ) TYPE: Amino Acid
            ( D ) TOPOLOGY: Linear ( x i ) SEQUENCE DESCRIPTION: SEQ ID NO:10:

Trp Ala Ser Gly Asn Gly Gly
 1              5         7

( 2 ) INFORMATION FOR SEQ ID NO:11:

( i ) SEQUENCE CHARACTERISTICS:
            ( A ) LENGTH: 7 amino acids
            ( B ) TYPE: Amino Acid
            ( D ) TOPOLOGY: Linear ( x i ) SEQUENCE DESCRIPTION: SEQ ID NO:11:

Cys Asn Cys Asp Gly Tyr Thr
 1              5         7

( 2 ) INFORMATION FOR SEQ ID NO:12:

( i ) SEQUENCE CHARACTERISTICS:
            ( A ) LENGTH: 7 amino acids
            ( B ) TYPE: Amino Acid
            ( D ) TOPOLOGY: Linear ( x i ) SEQUENCE DESCRIPTION: SEQ ID NO:12:

Trp Ala Ser Gly Asp Gly Gly
 1              5         7

( 2 ) INFORMATION FOR SEQ ID NO:13:

( i ) SEQUENCE CHARACTERISTICS:
            ( A ) LENGTH: 7 amino acids
            ( B ) TYPE: Amino Acid
            ( D ) TOPOLOGY: Linear ( x i ) SEQUENCE DESCRIPTION: SEQ ID NO:13:

Cys Asn Cys Asp Gly Tyr Ala
 1              5         7

( 2 ) INFORMATION FOR SEQ ID NO:14:

( i ) SEQUENCE CHARACTERISTICS:
            ( A ) LENGTH: 6 amino acids
            ( B ) TYPE: Amino Acid
            ( D ) TOPOLOGY: Linear ( x i ) SEQUENCE DESCRIPTION: SEQ ID NO:14:

Val Ile Asp Ser Gly Ile
 1              5    6

( 2 ) INFORMATION FOR SEQ ID NO:15:

( i ) SEQUENCE CHARACTERISTICS:
            ( A ) LENGTH: 5 amino acids
            ( B ) TYPE: Amino Acid
            ( D ) TOPOLOGY: Linear ( x i ) SEQUENCE DESCRIPTION: SEQ ID NO:15:

Asp Asn Asn Ser His
 1              5

( 2 ) INFORMATION FOR SEQ ID NO:16:

( i ) SEQUENCE CHARACTERISTICS:
   ( A ) LENGTH: 6 amino acids
   ( B ) TYPE: Amino Acid
   ( D ) TOPOLOGY: Linear ( x i ) SEQUENCE DESCRIPTION: SEQ ID NO:16:

Ile Val Asp Asp Gly Leu
 1           5   6

( 2 ) INFORMATION FOR SEQ ID NO:17:

( i ) SEQUENCE CHARACTERISTICS:
      ( A ) LENGTH: 5 amino acids
      ( B ) TYPE: Amino Acid
      ( D ) TOPOLOGY: Linear ( x i ) SEQUENCE DESCRIPTION: SEQ ID NO:17:

Ser Asp Asp Tyr His
 1           5

( 2 ) INFORMATION FOR SEQ ID NO:18:

( i ) SEQUENCE CHARACTERISTICS:
      ( A ) LENGTH: 6 amino acids
      ( B ) TYPE: Amino Acid
      ( D ) TOPOLOGY: Linear ( x i ) SEQUENCE DESCRIPTION: SEQ ID NO:18:

Ile Leu Asp Asp Gly Ile
 1           5   6

( 2 ) INFORMATION FOR SEQ ID NO:19:

( i ) SEQUENCE CHARACTERISTICS:
      ( A ) LENGTH: 5 amino acids
      ( B ) TYPE: Amino Acid
      ( D ) TOPOLOGY: Linear ( x i ) SEQUENCE DESCRIPTION: SEQ ID NO:19:

Asn Asp Asn Arg His
 1           5

( 2 ) INFORMATION FOR SEQ ID NO:20:

( i ) SEQUENCE CHARACTERISTICS:
      ( A ) LENGTH: 6 amino acids
      ( B ) TYPE: Amino Acid
      ( D ) TOPOLOGY: Linear ( x i ) SEQUENCE DESCRIPTION: SEQ ID NO:20:

Ile Met Asp Asp Gly Ile
 1           5   6

( 2 ) INFORMATION FOR SEQ ID NO:21:

( i ) SEQUENCE CHARACTERISTICS:
      ( A ) LENGTH: 5 amino acids
      ( B ) TYPE: Amino Acid
      ( D ) TOPOLOGY: Linear ( x i ) SEQUENCE DESCRIPTION: SEQ ID NO:21:

Trp Phe Asn Ser His
 1           5

( 2 ) INFORMATION FOR SEQ ID NO:22:

( i ) SEQUENCE CHARACTERISTICS:

(A) LENGTH: 27 base pairs
(B) TYPE: Nucleic Acid
(C) STRANDEDNESS: Single
(D) TOPOLOGY: Linear (xi) SEQUENCE DESCRIPTION: SEQ ID NO:22:

GCGGTTATCG ACGACGGTAT CGATTCT 27

(2) INFORMATION FOR SEQ ID NO:23:

(i) SEQUENCE CHARACTERISTICS:
(A) LENGTH: 27 base pairs
(B) TYPE: Nucleic Acid
(C) STRANDEDNESS: Single
(D) TOPOLOGY: Linear (xi) SEQUENCE DESCRIPTION: SEQ ID NO:23:

GCGGTTATCG ACAAAGGTAT CGATTCT 27

(2) INFORMATION FOR SEQ ID NO:24:

(i) SEQUENCE CHARACTERISTICS:
(A) LENGTH: 27 base pairs
(B) TYPE: Nucleic Acid
(C) STRANDEDNESS: Single
(D) TOPOLOGY: Linear (xi) SEQUENCE DESCRIPTION: SEQ ID NO:24:

GCGGTTATCG ACGAAGGTAT CGATTCT 27

(2) INFORMATION FOR SEQ ID NO:25:

(i) SEQUENCE CHARACTERISTICS:
(A) LENGTH: 23 base pairs
(B) TYPE: Nucleic Acid
(C) STRANDEDNESS: Single
(D) TOPOLOGY: Linear (xi) SEQUENCE DESCRIPTION: SEQ ID NO:25:

CCAAGACAAC GACTCTCACG GAA 23

(2) INFORMATION FOR SEQ ID NO:26:

(i) SEQUENCE CHARACTERISTICS:
(A) LENGTH: 23 base pairs
(B) TYPE: Nucleic Acid
(C) STRANDEDNESS: Single
(D) TOPOLOGY: Linear (xi) SEQUENCE DESCRIPTION: SEQ ID NO:26:

CCAAGACAAC AGCTCTCACG GAA 23

(2) INFORMATION FOR SEQ ID NO:27:

(i) SEQUENCE CHARACTERISTICS:
(A) LENGTH: 23 base pairs
(B) TYPE: Nucleic Acid
(C) STRANDEDNESS: Single
(D) TOPOLOGY: Linear (xi) SEQUENCE DESCRIPTION: SEQ ID NO:27:

CCAAGACAAC AAATCTCACG GAA 23

(2) INFORMATION FOR SEQ ID NO:28:

(i) SEQUENCE CHARACTERISTICS:
(A) LENGTH: 42 base pairs
(B) TYPE: Nucleic Acid (C) STRANDEDNESS: Single
(D) TOPOLOGY: Linear (xi) SEQUENCE DESCRIPTION: SEQ ID NO:28:

CACTTCCGGC AGCTCGTCGA CAGTGGACTA CCCTGGCAAA TA  42

(2) INFORMATION FOR SEQ ID NO:29:

(i) SEQUENCE CHARACTERISTICS:
(A) LENGTH: 42 base pairs
(B) TYPE: Nucleic Acid
(C) STRANDEDNESS: Single
(D) TOPOLOGY: Linear (xi) SEQUENCE DESCRIPTION: SEQ ID NO:29:

CACTTCCGGC AGCTCGTCGA CAGTGGAGTA CCCTGGCAAA TA  42

(2) INFORMATION FOR SEQ ID NO:30:

(i) SEQUENCE CHARACTERISTICS:
(A) LENGTH: 41 base pairs
(B) TYPE: Nucleic Acid
(C) STRANDEDNESS: Single
(D) TOPOLOGY: Linear (xi) SEQUENCE DESCRIPTION: SEQ ID NO:30:

TTAACATGAG CCTCGGCCCA GCTAGCGGTT CTGCTGCTTT A  41

(2) INFORMATION FOR SEQ ID NO:31:

(i) SEQUENCE CHARACTERISTICS:
(A) LENGTH: 43 base pairs
(B) TYPE: Nucleic Acid
(C) STRANDEDNESS: Single
(D) TOPOLOGY: Linear (xi) SEQUENCE DESCRIPTION: SEQ ID NO:31:

TTAACATGAG CCTCGGCCCC GCGGATGATT CTGCTGCTTT AAA  43

(2) INFORMATION FOR SEQ ID NO:32:

(i) SEQUENCE CHARACTERISTICS:
(A) LENGTH: 47 base pairs
(B) TYPE: Nucleic Acid
(C) STRANDEDNESS: Single
(D) TOPOLOGY: Linear (xi) SEQUENCE DESCRIPTION: SEQ ID NO:32:

CGGCAGCTCA AGCAACGATG GCTATCCTGG CAAATACCCT TCTGTCA  47

(2) INFORMATION FOR SEQ ID NO:33:

(i) SEQUENCE CHARACTERISTICS:
(A) LENGTH: 44 base pairs
(B) TYPE: Nucleic Acid
(C) STRANDEDNESS: Single
(D) TOPOLOGY: Linear (xi) SEQUENCE DESCRIPTION: SEQ ID NO:33:

ACTTCCGGCA GCTCTTCGAA CTACGACGGG TACCTGGCA AATA  44

(2) INFORMATION FOR SEQ ID NO:34:

(i) SEQUENCE CHARACTERISTICS:
(A) LENGTH: 5 amino acids
(B) TYPE: Amino Acid
(D) TOPOLOGY: Linear ( x i ) SEQUENCE DESCRIPTION: SEQ ID NO:34:

Asn Leu Thr Ala Arg
 1                    5

( 2 ) INFORMATION FOR SEQ ID NO:35:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:35:

Asn Leu Met Arg Lys
 1                    5

( 2 ) INFORMATION FOR SEQ ID NO:36:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:36:

Thr Ala Ser Arg Arg
 1                    5

( 2 ) INFORMATION FOR SEQ ID NO:37:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:37:

Leu Thr Arg Arg Ser
 1                    5

( 2 ) INFORMATION FOR SEQ ID NO:38:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:38:

Ala Leu Ser Arg Lys
 1                    5

( 2 ) INFORMATION FOR SEQ ID NO:39:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:39:

Leu Met Leu Arg Lys
 1                    5

( 2 ) INFORMATION FOR SEQ ID NO:40:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:40:

Ala Ser Thr His Phe
1               5

( 2 ) INFORMATION FOR SEQ ID NO:41:

( i ) SEQUENCE CHARACTERISTICS:
         ( A ) LENGTH: 5 amino acids
         ( B ) TYPE: Amino Acid
         ( D ) TOPOLOGY: Linear ( x i ) SEQUENCE DESCRIPTION: SEQ ID NO:41:

Gln Lys Pro Asn Phe
1               5

( 2 ) INFORMATION FOR SEQ ID NO:42:

( i ) SEQUENCE CHARACTERISTICS:
         ( A ) LENGTH: 5 amino acids
         ( B ) TYPE: Amino Acid
         ( D ) TOPOLOGY: Linear ( x i ) SEQUENCE DESCRIPTION: SEQ ID NO:42:

Arg Lys Pro Thr His
1               5

( 2 ) INFORMATION FOR SEQ ID NO:43:

( i ) SEQUENCE CHARACTERISTICS:
         ( A ) LENGTH: 5 amino acids
         ( B ) TYPE: Amino Acid
         ( D ) TOPOLOGY: Linear ( x i ) SEQUENCE DESCRIPTION: SEQ ID NO:43:

Ile Gln Gln Gln Tyr
1               5

( 2 ) INFORMATION FOR SEQ ID NO:44:

( i ) SEQUENCE CHARACTERISTICS:
         ( A ) LENGTH: 5 amino acids
         ( B ) TYPE: Amino Acid
         ( D ) TOPOLOGY: Linear ( x i ) SEQUENCE DESCRIPTION: SEQ ID NO:44:

Arg Pro Gly Ala Met
1               5

( 2 ) INFORMATION FOR SEQ ID NO:45:

( i ) SEQUENCE CHARACTERISTICS:
         ( A ) LENGTH: 5 amino acids
         ( B ) TYPE: Amino Acid
         ( D ) TOPOLOGY: Linear ( x i ) SEQUENCE DESCRIPTION: SEQ ID NO:45:

Gln Gly Glu Leu Pro
1               5

( 2 ) INFORMATION FOR SEQ ID NO:46:

( i ) SEQUENCE CHARACTERISTICS:
         ( A ) LENGTH: 5 amino acids
         ( B ) TYPE: Amino Acid
         ( D ) TOPOLOGY: Linear ( x i ) SEQUENCE DESCRIPTION: SEQ ID NO:46:

Ala Pro Asp Pro Thr
1               5

( 2 ) INFORMATION FOR SEQ ID NO:47:

( i ) SEQUENCE CHARACTERISTICS:
    ( A ) LENGTH: 5 amino acids
    ( B ) TYPE: Amino Acid
    ( D ) TOPOLOGY: Linear ( x i ) SEQUENCE DESCRIPTION: SEQ ID NO:47:

Gln Leu Leu Glu His
1               5

( 2 ) INFORMATION FOR SEQ ID NO:48:

( i ) SEQUENCE CHARACTERISTICS:
    ( A ) LENGTH: 5 amino acids
    ( B ) TYPE: Amino Acid
    ( D ) TOPOLOGY: Linear ( x i ) SEQUENCE DESCRIPTION: SEQ ID NO:48:

Val Asn Asn Asn His
1               5

( 2 ) INFORMATION FOR SEQ ID NO:49:

( i ) SEQUENCE CHARACTERISTICS:
    ( A ) LENGTH: 5 amino acids
    ( B ) TYPE: Amino Acid
    ( D ) TOPOLOGY: Linear ( x i ) SEQUENCE DESCRIPTION: SEQ ID NO:49:

Ala Gln Ser Asn Leu
1               5

( 2 ) INFORMATION FOR SEQ ID NO:50:

( i ) SEQUENCE CHARACTERISTICS:
    ( A ) LENGTH: 5 amino acids
    ( B ) TYPE: Amino Acid
    ( D ) TOPOLOGY: Linear ( x i ) SEQUENCE DESCRIPTION: SEQ ID NO:50:

Thr Ala Ser Arg Arg
1               5

( 2 ) INFORMATION FOR SEQ ID NO:51:

( i ) SEQUENCE CHARACTERISTICS:
    ( A ) LENGTH: 6 amino acids
    ( B ) TYPE: Amino Acid
    ( D ) TOPOLOGY: Linear ( x i ) SEQUENCE DESCRIPTION: SEQ ID NO:51:

His His His His His His
1               5   6

( 2 ) INFORMATION FOR SEQ ID NO:52:

( i ) SEQUENCE CHARACTERISTICS:
    ( A ) LENGTH: 4 amino acids
    ( B ) TYPE: Amino Acid
    ( D ) TOPOLOGY: Linear ( x i ) SEQUENCE DESCRIPTION: SEQ ID NO:52:

Leu Met Arg Lys
1           4

( 2 ) INFORMATION FOR SEQ ID NO:53:

( i ) SEQUENCE CHARACTERISTICS:
        ( A ) LENGTH: 4 amino acids
        ( B ) TYPE: Amino Acid
        ( D ) TOPOLOGY: Linear ( x i ) SEQUENCE DESCRIPTION: SEQ ID NO:53:

Leu Thr Ala Arg
1             4

( 2 ) INFORMATION FOR SEQ ID NO:54:

( i ) SEQUENCE CHARACTERISTICS:
        ( A ) LENGTH: 4 amino acids
        ( B ) TYPE: Amino Acid
        ( D ) TOPOLOGY: Linear ( x i ) SEQUENCE DESCRIPTION: SEQ ID NO:54:

Gly Pro Gly Gly
1             4

( 2 ) INFORMATION FOR SEQ ID NO:55:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:55:

Gly Leu Met Arg Lys
1                 5

( 2 ) INFORMATION FOR SEQ ID NO:56:

( i ) SEQUENCE CHARACTERISTICS:
        ( A ) LENGTH: 4 amino acids
        ( B ) TYPE: Amino Acid
        ( D ) TOPOLOGY: Linear ( x i ) SEQUENCE DESCRIPTION: SEQ ID NO:56:

Ala Ala Pro Phe
1             4

( 2 ) INFORMATION FOR SEQ ID NO:57:

( i ) SEQUENCE CHARACTERISTICS:
        ( A ) LENGTH: 13 amino acids
        ( B ) TYPE: Amino Acid
        ( D ) TOPOLOGY: Linear ( x i ) SEQUENCE DESCRIPTION: SEQ ID NO:57:

Gly Pro Gly Gly Xaa Xaa Xaa Xaa Xaa Gly Gly Pro Gly
1               5                   10            13

( 2 ) INFORMATION FOR SEQ ID NO:58:

( i ) SEQUENCE CHARACTERISTICS:
        ( A ) LENGTH: 4 amino acids
        ( B ) TYPE: Amino Acid
        ( D ) TOPOLOGY: Linear ( x i ) SEQUENCE DESCRIPTION: SEQ ID NO:58:

Ala Ala Pro Lys
1             4

( 2 ) INFORMATION FOR SEQ ID NO:59:

( i ) SEQUENCE CHARACTERISTICS:
    ( A ) LENGTH: 4 amino acids
    ( B ) TYPE: Amino Acid
    ( D ) TOPOLOGY: Linear ( x i ) SEQUENCE DESCRIPTION: SEQ ID NO:59:

Ala Ala Pro Arg
1            4

( 2 ) INFORMATION FOR SEQ ID NO:60:

( i ) SEQUENCE CHARACTERISTICS:
        ( A ) LENGTH: 4 amino acids
        ( B ) TYPE: Amino Acid
        ( D ) TOPOLOGY: Linear ( x i ) SEQUENCE DESCRIPTION: SEQ ID NO:60:

Ala Ala Pro Met
1            4

( 2 ) INFORMATION FOR SEQ ID NO:61:

( i ) SEQUENCE CHARACTERISTICS:
        ( A ) LENGTH: 4 amino acids
        ( B ) TYPE: Amino Acid
        ( D ) TOPOLOGY: Linear ( x i ) SEQUENCE DESCRIPTION: SEQ ID NO:61:

Ala Ala Pro Gln
1            4

( 2 ) INFORMATION FOR SEQ ID NO:62:

( i ) SEQUENCE CHARACTERISTICS:
        ( A ) LENGTH: 4 amino acids
        ( B ) TYPE: Amino Acid
        ( D ) TOPOLOGY: Linear ( x i ) SEQUENCE DESCRIPTION: SEQ ID NO:62:

Ala Ala Lys Phe
1            4

( 2 ) INFORMATION FOR SEQ ID NO:63:

( i ) SEQUENCE CHARACTERISTICS:
        ( A ) LENGTH: 4 amino acids
        ( B ) TYPE: Amino Acid
        ( D ) TOPOLOGY: Linear ( x i ) SEQUENCE DESCRIPTION: SEQ ID NO:63:

Ala Ala Ala Phe
1            4

( 2 ) INFORMATION FOR SEQ ID NO:64:

( i ) SEQUENCE CHARACTERISTICS:
        ( A ) LENGTH: 4 amino acids
        ( B ) TYPE: Amino Acid
        ( D ) TOPOLOGY: Linear ( x i ) SEQUENCE DESCRIPTION: SEQ ID NO:64:

Ala Ala Arg Phe
1            4

( 2 ) INFORMATION FOR SEQ ID NO:65:

( i ) SEQUENCE CHARACTERISTICS:
        ( A ) LENGTH: 4 amino acids (B) TYPE: Amino Acid
(D) TOPOLOGY: Linear (xi) SEQUENCE DESCRIPTION: SEQ ID NO:65:

Ala Ala Asp Phe
1           4

(2) INFORMATION FOR SEQ ID NO:66:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO:66:

Ala Ala Lys Lys
1           4

(2) INFORMATION FOR SEQ ID NO:67:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO:67:

Ala Ala Lys Arg
1           4

(2) INFORMATION FOR SEQ ID NO:68:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO:68:

Ala Ala Lys Phe
1           4

(2) INFORMATION FOR SEQ ID NO:69:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO:69:

Ala Ala Pro Xaa
1           4

(2) INFORMATION FOR SEQ ID NO:70:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO:70:

Ala Ala Xaa Phe
1           4

(2) INFORMATION FOR SEQ ID NO:71:

(i) SEQUENCE CHARACTERISTICS:
(A) LENGTH: 5 amino acids
(B) TYPE: Amino Acid
(D) TOPOLOGY: Linear ( x i ) SEQUENCE DESCRIPTION: SEQ ID NO:71:

Ala Ala Xaa Xaa Xaa
 1           5

( 2 ) INFORMATION FOR SEQ ID NO:72:

( i ) SEQUENCE CHARACTERISTICS:
        ( A ) LENGTH: 275 amino acids
        ( B ) TYPE: Amino Acid
        ( D ) TOPOLOGY: Linear ( x i ) SEQUENCE DESCRIPTION: SEQ ID NO:72:

```
Ala Gln Ser Val Pro Tyr Gly Val Ser Gln Ile Lys Ala Pro Ala
 1           5                  10                      15
Leu His Ser Gln Gly Tyr Thr Gly Ser Asn Val Lys Val Ala Val
            20                  25                      30
Ile Asp Ser Gly Ile Asp Ser Ser His Pro Asp Leu Lys Val Ala
            35                  40                      45
Gly Gly Ala Ser Met Val Pro Ser Glu Thr Asn Pro Phe Gln Asp
            50                  55                      60
Asn Asp Ser His Gly Thr His Val Ala Gly Thr Val Ala Ala Leu
            65                  70                      75
Asn Asn Ser Ile Gly Val Leu Gly Val Ala Pro Ser Ala Ser Leu
            80                  85                      90
Tyr Ala Val Lys Val Leu Gly Ala Asp Gly Ser Gly Gln Tyr Ser
            95                  100                     105
Trp Ile Ile Asn Gly Ile Glu Trp Ala Ile Ala Asn Asn Met Asp
            110                 115                     120
Val Ile Asn Met Ser Leu Gly Gly Pro Ser Gly Ser Ala Ala Leu
            125                 130                     135
Lys Ala Ala Val Asp Lys Ala Val Ala Ser Gly Val Val Val Val
            140                 145                     150
Ala Ala Ala Gly Asn Glu Gly Thr Ser Gly Ser Ser Ser Thr Val
            155                 160                     165
Asp Tyr Pro Gly Lys Tyr Pro Ser Val Ile Ala Val Gly Ala Val
            170                 175                     180
Asp Ser Ser Asn Gln Arg Ala Ser Phe Ser Ser Val Gly Pro Glu
            185                 190                     195
Leu Asp Val Met Ala Pro Gly Val Ser Ile Gln Ser Thr Leu Pro
            200                 205                     210
Gly Asn Lys Tyr Gly Ala Tyr Asn Gly Thr Ser Met Ala Ser Pro
            215                 220                     225
His Val Ala Gly Ala Ala Ala Leu Ile Leu Ser Lys His Pro Asn
            230                 235                     240
Trp Thr Asn Thr Gln Val Arg Ser Ser Leu Glu Asn Thr Thr Thr
            245                 250                     255
Lys Leu Gly Asp Ser Phe Tyr Tyr Gly Lys Gly Leu Ile Asn Val
            260                 265                     270
Gln Ala Ala Ala Gln
            275
```

( 2 ) INFORMATION FOR SEQ ID NO:73:

( i ) SEQUENCE CHARACTERISTICS:
        ( A ) LENGTH: 4 amino acids
        ( B ) TYPE: Amino Acid
        ( D ) TOPOLOGY: Linear ( x i ) SEQUENCE DESCRIPTION: SEQ ID NO:73:

Arg Val Arg Arg
 1           4

( 2 ) INFORMATION FOR SEQ ID NO:74:

( i ) SEQUENCE CHARACTERISTICS:
( A ) LENGTH: 275 amino acids
( B ) TYPE: Amino Acid
( D ) TOPOLOGY: Linear ( x i ) SEQUENCE DESCRIPTION: SEQ ID NO:74:

```
Ala Gln Ser Val Pro Tyr Gly Val Ser Gln Ile Lys Ala Pro Ala
 1               5                   10                  15

Leu His Ser Gln Gly Tyr Thr Gly Ser Asn Val Lys Val Ala Val
                 20                  25                  30

Ile Asp Ser Gly Ile Asp Ser Ser His Pro Asp Leu Lys Val Ala
                 35                  40                  45

Gly Gly Ala Ser Met Val Pro Ser Glu Thr Asn Pro Phe Gln Asp
                 50                  55                  60

Asn Asn Ser His Gly Thr His Val Ala Gly Thr Val Ala Ala Leu
                 65                  70                  75

Asn Asn Ser Ile Gly Val Leu Gly Val Ala Pro Ser Ala Ser Leu
                 80                  85                  90

Tyr Ala Val Lys Val Leu Gly Ala Asp Gly Ser Gly Gln Tyr Ser
                 95                 100                 105

Trp Ile Ile Asn Gly Ile Glu Trp Ala Ile Ala Asn Asn Met Asp
                110                 115                 120

Val Ile Asn Met Ser Leu Gly Gly Pro Ser Gly Ser Ala Ala Leu
                125                 130                 135

Lys Ala Ala Val Asp Lys Ala Val Ala Ser Gly Val Val Val Val
                140                 145                 150

Ala Ala Ala Gly Asn Glu Gly Thr Ser Gly Ser Ser Ser Thr Val
                155                 160                 165

Gly Tyr Pro Gly Lys Tyr Pro Ser Val Ile Ala Val Gly Ala Val
                170                 175                 180

Asp Ser Ser Asn Gln Arg Ala Ser Phe Ser Ser Val Gly Pro Glu
                185                 190                 195

Leu Asp Val Met Ala Pro Gly Val Ser Ile Gln Ser Thr Leu Pro
                200                 205                 210

Gly Asn Lys Tyr Gly Ala Tyr Asn Gly Thr Ser Met Ala Ser Pro
                215                 220                 225

His Val Ala Gly Ala Ala Ala Leu Ile Leu Ser Lys His Pro Asn
                230                 235                 240

Trp Thr Asn Thr Gln Val Arg Ser Ser Leu Glu Asn Thr Thr Thr
                245                 250                 255

Lys Leu Gly Asp Ser Phe Tyr Tyr Gly Lys Gly Leu Ile Asn Val
                260                 265                 270

Gln Ala Ala Ala Gln
                275
```

SUBTILISIN VARIANTS CAPABLE OF CLEAVING SUBSTRATES CONTAINING DIBASIC RESIDUES

This is a continuation of co-pending application Ser. No. 08/398,028 filed on 3 Mar. 1995, which application is incorporated herein by reference and to which application priority is claimed under 35 USC 120.

FIELD OF THE INVENTION

This invention relates to subtilisin variants having altered specificity from wild-type subtilisin useful for processing fusion proteins, especially those made in recombinant cell culture. Specifically, the subtilisin variants are modified so that they efficiently and selectively cleave substrates containing dibasic residues.

BACKGROUND OF THE INVENTION

Site-specific proteolysis is one of the most common forms of post-translational modifications of proteins (for review see Neurath, H. [1989] *Trends Biochem. Sci.*, 14:268). In addition, proteolysis of fusion proteins in vitro is an important research and commercial tool (for reviews see Uhlen, M. and Moks, T. [1990] *Methods Enzymol.*, 185:129-143; Carter, P. [1990] in *Protein Purification: From Molecular Mechanisms to Large-Scale Processes*, M. R. Landisch, R. C. Wilson, C. D. Painton, S. E. Builder, Eds. [ACS Symposium Series 427, American Chemical Society, Washington, D.C.], Chap. 13, p.181–193; and Nilsson, B. et al. [1992] *Current Opin. Struct. Biol.*, 2:569). Expressing a protein of interest as a fusion protein facilitates purification when the fusion contains an affinity domain such as glutathione-S-transferase, Protein A or a poly-histidine tail. The fusion domain can also facilitate high level expression and/or secretion.

To liberate the protein product from the fusion domain requires selective and efficient cleavage of the fusion protein. Both chemical and enzymatic methods have been proposed (see references above). Enzymatic methods are generally preferred as they tend to be more specific and can be performed under mild conditions that avoid denaturation or unwanted chemical side-reactions. A number of natural and even designed enzymes have been applied for site-specific proteolysis. Although some are generally more useful than others (Forsberg, G., Baastrup, B., Rondahl, H., Holmgren, E., Pohl, G., Hartmanis, M. and Lake, M. [1992] *J. Prot. Chem.*, 11:201–211), no one is applicable to every situation given the sequence requirements of the fusion protein junction and the possible existence of protease sequences within the desired protein product. Thus, an expanded array of sequence specific proteases, analogous to restriction endonucleases, would make site-specific proteolysis a more widely used method for processing fusion proteins or generating protein/peptide fragments either in vitro or in vivo.

One of the most popular site-specific proteolysis events is the maturation of pro-hormones by the KEX2-family of enzymes that are present in eukaryotic cells (for reviews see Steiner, D. F., Smeekens, S. P., Ohagi, S. and Chan, S. J. [1992] *J. Biol. Chem.*, 267:23435–23438 and Smeekens, S. P. [1993] *Bio/Technology*, 11:182–186). This family of proteases, that includes the yeast KEX2 and the mammalian PC2 and furin enzymes, are homologous to the bacterial serine protease subtilisin (Kraut, J. [1977] *Annu. Rev. Biochem.*, 46:331–358). Subtilisin has a broad substrate specificity that reflects its role as a scavenger protease. In contrast, these eukaryotic enzymes are very specific for cleaving substrates containing two basic residues and thus well-suited for site-specific proteolysis. However, the eukaryotic proteases are expressed in small amounts (Bravo, D. B., Gleason, J. B., Sanchez, R. I., Roth, R. A., and Fuller, R. S. [1994] *J. Biol. Chem.*, 269:25830–25837 and Matthews, D. J., Goodman, L. J., Gorman, C. M., and Wells, J. A. [1994] *Protein Science*, 3:1197–1205) making them impractical to apply presently to processing of fusion proteins in vitro.

Despite the very narrow specificity of the pro-hormone processing enzymes, in some cases they are capable of rapid cleavage of target sequences. For example, the $k_{cat}/Km$ ratio for KEX2 to cleave a good substrate (e.g. Boc-RVRR-MCA) is $1 \times 10^6 \, M^{-1} s^{-1}$ (Brenner, C., and Fuller, R. S. [1992] *Proc. Natl. Acad. Sci. USA*, 89:922–926) compared to $3 \times 10^5$ for subtilisin cleaving a good substrate (e.g. suc-AAPF-pna) (Estell, D. A., Graycar, T. P., Miller, J. V., Powers, D. B., Burnier, J. P., Ng, P. G. and Wells, J. A. [1986] *Science*, 233:659–663). Given the fact that subtilisin BPN' can be expressed in large amounts (Wells, J. A., Ferrari, E., Henner, D. J., Estell, D. A. and Chen, E. Y. [1983] *Nucl. Acids Res.*, 11:7911–7929) we wondered if it would be possible to engineer the specificity of subtilisin to be like that of KEX2, to produce a useful subtilisin variant for processing fusion proteins or generating protein fragments by cleavage at designed dibasic sites.

Previous attempts to introduce or reverse charge specificity in enzyme active sites have been met with considerable difficulty. This has generally been attributed to a lack of stabilization of the introduced charge or enzyme-substrate ion pair complex by the wild-type enzyme environment (Hwang, J. K. and Warshel, A. [1988] *Nature*, 334:270–272). For example, Stennicke et. al (Stennicke, H. R.; Ujje, H. M.; Christensen, U.; Remington, S. J.; and Breddam [1994] *Prot. Eng.* 7:911–916) made acidic (D/E) mutations at five residues in the P1' binding of carboxypeptidase Y in an attempt to change the P1' preference from Phe to Lys/Arg. Only the L272D and L272E mutations were found to alter the specificity in the desired direction, up to 1.5-fold preference in Lys/Arg over Phe, and the others simply resulted in less active enzymes having substrate preferences similar to wild-type. In the case of trypsin, a protease that is highly specific for basic P1 residues, recruitment of chymotrypsin-like (hydrophobic P1) specificity required not only mutations of the ion pair-forming Asp 189 to Ser, but also transplantation of two more distant surface loops from chymotrypsin (Graf, L., Jancso, A., Szilagyi, L., Hegyi, G., Pinter, K., Naray-Szabo, G., Hepp, J., Medzihradszky, K., and Rutter, W. J., *Proc. Natl. Acad. Sci. USA* [1988] 85:4961–4965 and Hedstrom, L., Szilagyi, L., and Rutter, W. J., *Science* [1992] 255:1249–1253).

In the present work, we have also verified that relatively low specificity is gained by introducing single ion-pairs between enzyme and substrate. However, when two choice ionic interactions were simultaneously engineered into subtilisin BPN', the resulting variant had higher specificity for basic residues in each of the subsites due to a non additive effect.

Accordingly, it is an object to produce a subtilisin variant with dibasic specificity for use in processing pro-proteins made by recombinant techniques.

SUMMARY OF THE INVENTION

The invention includes subtilisin variants, having a substrate specificity which is substantially different from the substrate specificity of the precursor subtilisin from which the amino acid sequence of the mutant is derived. The substrate specificity of the preferred subtilisin variants is for substrates having dibasic amino acid residues. The preferred precursor subtilisin is subtilisin from *Bacillus amyloliquefaciens*, referred to as subtilisin BPN'. The amino acid sequence of the subtilisin variants are derived by the substitution of one or more amino acids of the precursor subtilisin amino acid sequence. The preferred subtilisin variants having substrate specificity for dibasic substrates have a different amino acid residue at residue position +62 than subtilisin naturally produced by *Bacillus amyloliquefaciens*. The naturally occurring Asn (N) at residue position +62 of subtilisin BPN' is preferably substituted with an acidic amino acid residue such as Glu (E) or Asp (D), most preferably D. The most preferred subtilisin variants, having substrate specificity for substrates having dibasic amino acid residues, additionally have an acidic residue, E or D, at residue position +62 of subtilisin BPN'. Thus the subtilisin BPN' variant N62D/G166D may be used to cleave fusion proteins with dibasic substrate linkers and processing hormones or other proteins (in vitro or in vivo) that contain dibasic cleavage sites.

Preferred substrates for the subtilisin BPN' variant N62D/G166D contain either Lys (K) or Arg (R) at substrate positions P2 and P1, practically any residue at P3, a non-charged hydrophobic residue at P4, and again practically any residue at P5. Thus an exemplary good substrate would contain -Asn-Leu-Met-Arg-Lys- (SEQ ID NO: 35) at -P5-P4-P3-P2-P1- respectively. Additionally, good substrates would not have Pro at P1', P2', or P3' nor would Ile be present at P1'. Thus the invention includes a process comprising contacting the subtilisin variant having substrate specificity for dibasic amino acid residues with a substrate containing the above described amino acid residues under conditions.

The invention also includes mutant DNA sequences encoding such subtilisin variants. These mutant DNA sequences are derived from a precursor DNA sequence which encodes a naturally occurring or recombinant precursor subtilisin. The mutant DNA sequence is derived by modifying the precursor DNA sequence to encode the substitution(s) of one or more amino acids encoded by the precursor DNA sequence. These recombinant DNA sequences encode mutants having an amino acid sequence which does not exist in nature and a substrate specificity which is substantially different from the substrate specificity of the precursor subtilisin encoded by the precursor DNA sequence.

Further the invention includes expression vectors containing such mutant DNA sequences as well as host cells transformed with such vectors which are capable of expressing the subtilisin variants.

BRIEF DESCRIPTION OF THE FIGURES

Figure 6A:
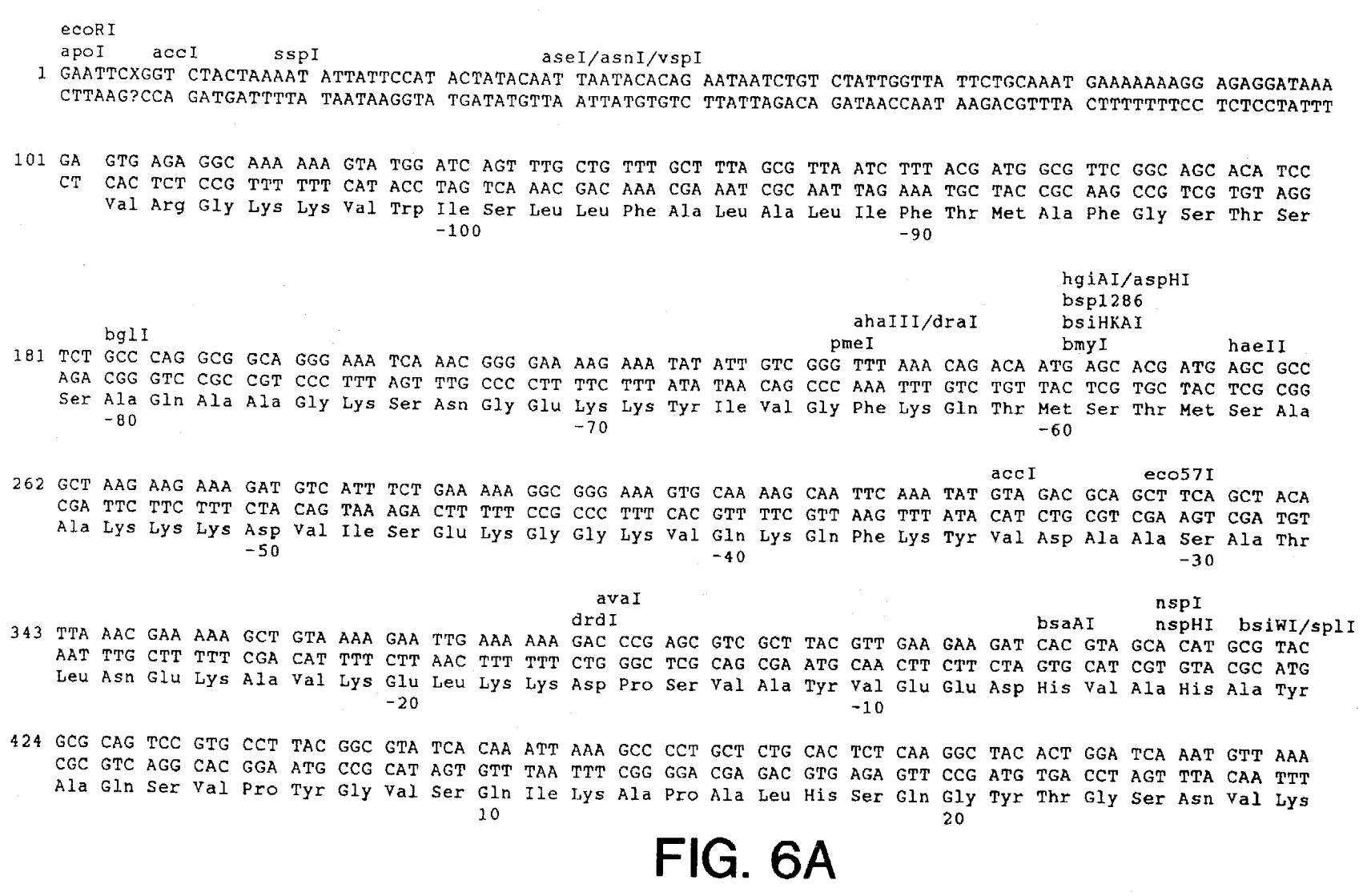

FIG. 6-A-6-N. (Collectively referred to herein as FIG. 6). DNA sequence of the phagemid pSS5 containing the N62D/G166D double mutant subtilisin BPN' gene (SEQ ID NO: 1), and translated amino acid sequence for the mutant preprosubtilisin (SEQ ID NO: 2). The pre region is comprised of residues −102 to −76, the pro of residues −75 to −1, and the mature enzyme of residues +1 to +275 (SEQ ID NO: 72). Also shown are restriction sites recognized by endonucleases that require 6 or more specific bases in succession.

DETAILED DESCRIPTION OF THE INVENTION

Definitions

Figure 1:
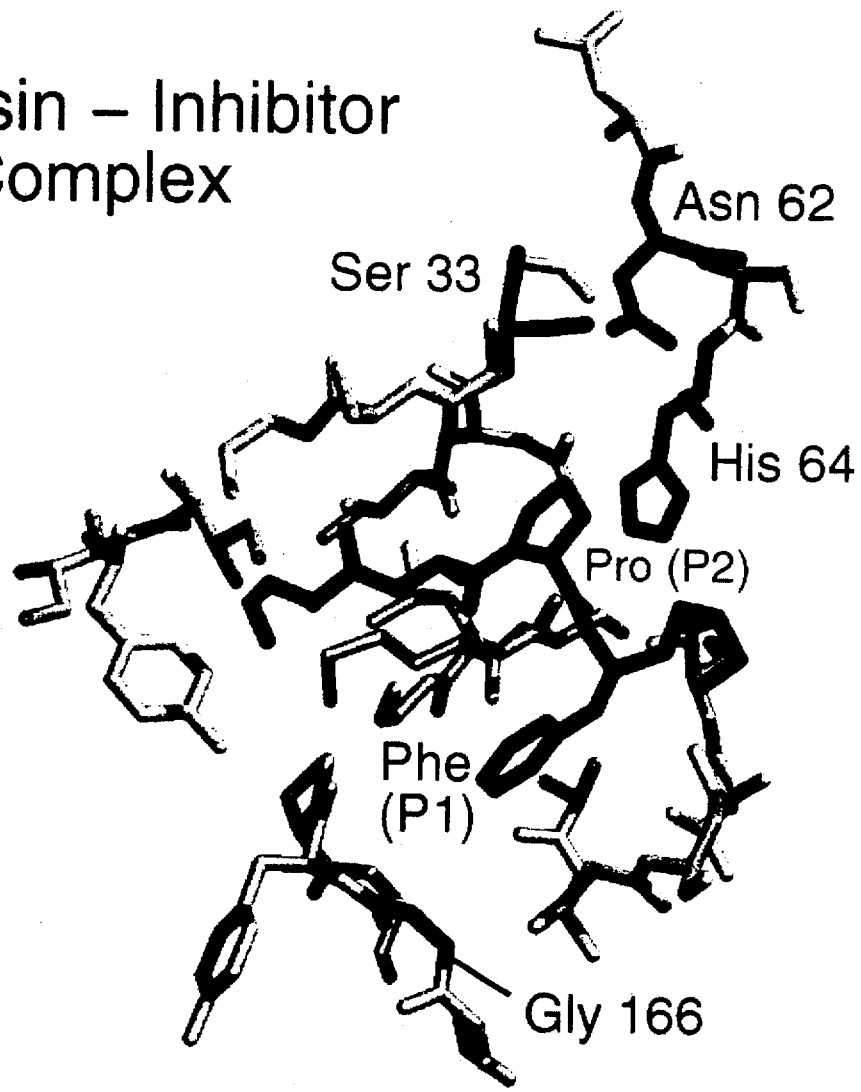
FIG. 1. Structure of a succinyl-Ala-Ala-Pro-BoroPhe (SEQ ID NO: 69) inhibitor bound to the active site of subtilisin BPN' showing the S2 and S1 binding pocket residues subjected to mutagenesis.

Terms used in the claims and specification are defined as set forth below unless otherwise specified.

The term amino acid or amino acid residue, as used herein, refers to naturally-occurring L α-amino acids or residues, unless otherwise specifically indicated. The commonly used one- and three-letter abbreviations for amino acids are use herein (Lehninger, A. L., *Biochemistry*, 2d ed., pp. 71–92, Worth Publishers, N. Y. [1975]).

Substrates are described in triplet or single letter code as Pn . . . P2-P1-P1'-P2' . . . Pn'. The "P1" residue refers to the position proceeding the scissile peptide bond (i.e. between the P1 and P1' residues) of the substrate as defined by Schechter and Berger (Schechter, I. and Berger, A., *Biochem. Biophys. Res. Commun.* 27: 157–162 [1967]).

"Subtilisins" are bacterial carbonyl hydrolases which generally act to cleave peptide bonds of proteins or peptides. As used herein, "subtilisin" means a naturally occurring subtilisin or a recombinant subtilisin. A series of naturally occurring subtilisins are known to be produced and often secreted by various bacterial species. Amino acid sequences of the members of this series are not entirely homologous. However, the subtilisins in this series exhibit the same or similar type of proteolytic activity. This class of serine proteases shares a common amino acid sequence defining a catalytic triad which distinguishes them from the chymotrypsin related class of serine proteases. The subtilisins and chymotrypsin related serine proteases both have a catalytic triad comprising aspartate, histidine and serine. In the subtilisin related proteases the relative order of these amino acids, reading from the amino to carboxy terminus is aspartate-histidine-serine. In the chymotrypsin related proteases the relative order, however is histidine-aspartate-serine. Thus, subtilisins as used herein refer to a serine protease having the catalytic triad of subtilisin related proteases.

Generally, subtilisins are serine endoproteases' having molecular weights of about 27,500 which are secreted in large amounts from a wide variety of Bacillus species. The protein sequence of subtilisins have been determined from at least four different species of Bacillus. Markland, F. S., et al. (1971) in *The Enzymes*, ed. Boyer P. D., Acad Press, New York, Vol. III, pp. 561–608 and Nedkov, P. et al. (1983) *Hoppe-Seyler's Z. Physiol. Chem.* 364:1537–1540. The three-dimensional crystallographic structure of subtilisin BPN' (from *B. amyloliquefaciens*) to 2.5A_ resolution has also been reported by Wright, C. S. et al. [1969] *Nature* 221:235–242 and Drenth, J. et al. [1972] *Eur. J. Biochem.* 26:177–181. These studies indicate that although subtilisin is genetically unrelated to the mammalian serine proteases, it has a similar active site structure. The x-ray crystal structures of subtilisin containing covalently bound peptide inhibitors (Robertus, J. D., et al. [1972] *Biochemistry* 11:2439–2449), product complexes (Robertus, J. D., et al. [1972] *Biochemistry* 11:4293–4303), and transition state analogs (Matthews, D. A., et al. [1975] *J. Biol. Chem.* 250:7120–7126 and Poulos, T. L., et al. [1976] *J. Biol. Chem.* 251:1097–1103), which have been reported have also provided information regarding the active site and putative substrate binding cleft of subtilisins. In addition, a large number of kinetic and chemical modification studies have been reported for subtilisins (Phillip, M., et al. [1983] *Mol. Cell. Biochem.* 51:5–32; Svendsen, I. B. [1976] *Carlsberg Res. Comm.* 41:237–291 and Markland, F. S. Id.) as well as at least one report wherein the side chain of methione at residue 222 of subtilisin was converted by hydrogen peroxide to methionine-sulfoxide (Stauffer, D. C., et al. [1965] *J. Biol. Chem.* 244:5333–5338).

"Recombinant subtilisin" refers to a subtilisin in which the DNA sequence encoding the subtilisin is modified to produce a mutant DNA sequence which encodes the substitution of one or more amino acids in the naturally occurring subtilisin amino acid-sequence. Suitable methods to produce such modification include those disclosed in U.S. Pat. Nos. 4,760,025 and 5,371,008 and in EPO Publication No. 0130756 and 0251446.

When referring to mutants or variants, the wild type amino acid residue is followed by the residue number and the new or substituted amino acid residue. For example, substitution of D for wild type N in residue position 62 is denominated N62D.

"Subtilisin variants or mutants" are designated in the same manner by using the single letter amino acid code for the wild-type residue followed by its position and the single letter amino acid code of the replacement residue. Multiple mutants are indicated by component single mutants separated by slashes. Thus the subtilisin BPN' variant N62D/G166D is a di-substituted variant in which Asp replaces Asn and Gly at residue positions 62 and 166 in wild-type subtilisin BPN'.

Specific residues of *B. amyloliquefaciens* subtilisin are identified for substitution. These amino acid residue position numbers refer to those assigned to the *B. amyloliquefaciens* subtilisin sequence (SEQ ID NO:74) (see the mature sequence in FIG. 1. of U.S. Pat. No. 4,760,025). The invention, however, is not limited to the mutation of this particular subtilisin but extends to precursor carbonyl hydrolases containing amino acid residues which are "equivalent" to the particular identified residues in *B. amyloliquefaciens* subtilisin. An amino acid residue of a precursor carbonyl hydrolase is "equivalent" to a residue of *B. amyloliquefaciens* subtilisin if it is either homologous (i.e., corresponding in position in either primary or tertiary structure) or analogous to a specific residue or portion of that residue in *B. amyloliquefaciens* subtilisin (i.e., having the same or similar functional capacity to combine, react, or interact chemically).

Figure 5:
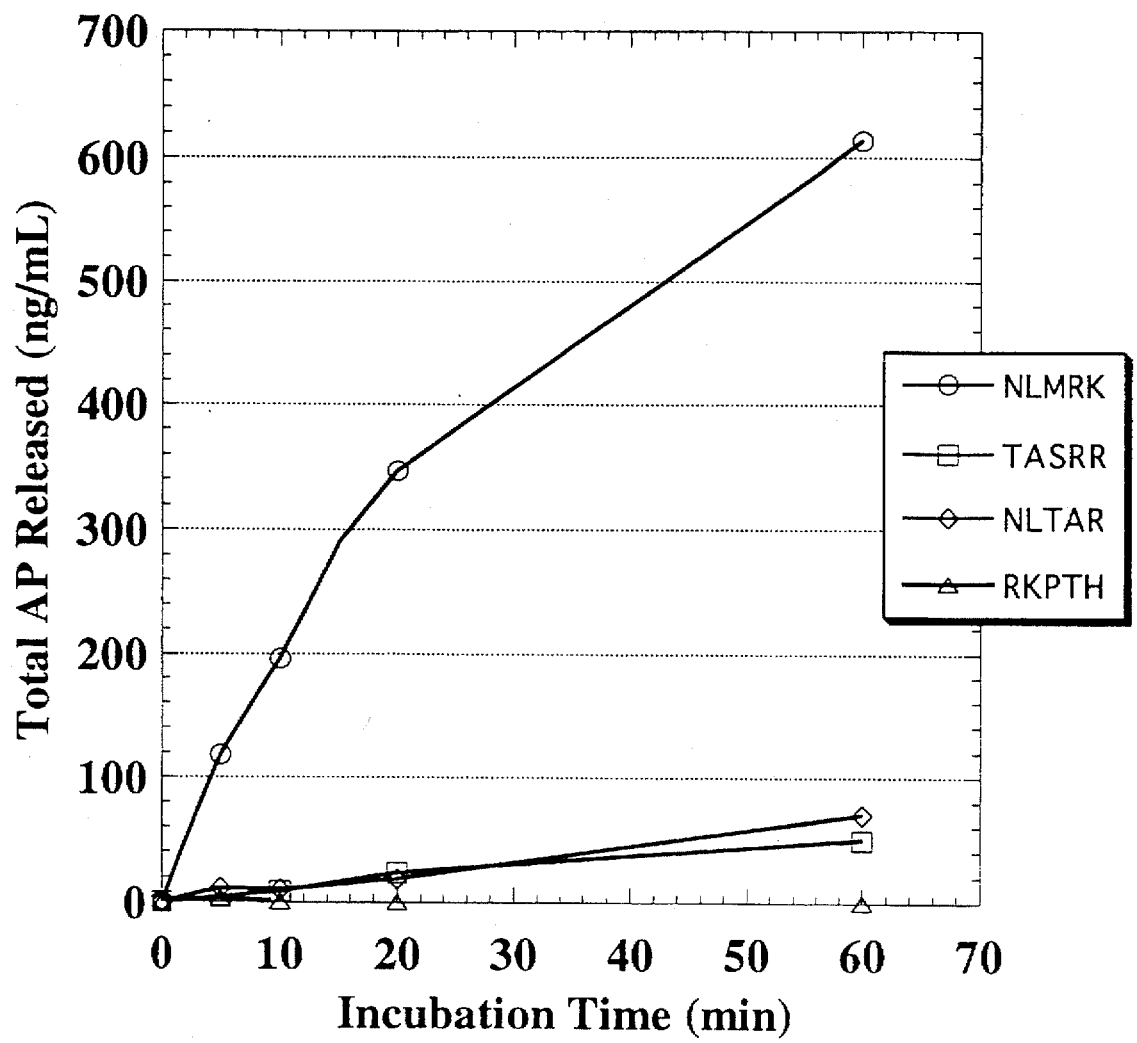
FIG. 5. Result s of hGH-AP fusion protein assay. hGH-AP fusion proteins were constructed, bound to hGHbp-coupled resin, and treated with 0.5 nM N62D/G166D subtilisin in 20 mM Tris-Cl pH 8.2. Aliquots were withdrawn at various times and AP release was monitored by activity assay in comparison to a standard curve as described (10, 19).

In order to establish homology to primary structure, the amino acid sequence of a precursor carbonyl hydrolase is directly compared to the *B. amyloliquefaciens* subtilisin primary sequence and particularly to a set of residues known to be invariant in all subtilisins for which the sequences are known (see e.g. FIG. 5-C in EPO 0251446). After aligning the conserved residues, allowing for necessary insertions and deletions in order to maintain alignment (i.e., avoiding the elimination of conserved residues through arbitrary deletion and insertion), the residues equivalent to particular amino acids in the primary sequence of *B. amyloliquefaciens* subtilisin are defined. Alignment of conserved residues should conserve 100% of such residues. However, alignment of greater than 75% or as little as 50% of conserved residues is also adequate to define equivalent residues. Conservation of the catalytic triad, Asp32/His64/Ser221, is required.

Equivalent residues homologous at the level of tertiary structure for a precursor carbonyl hydrolase whose tertiary structure has been determined by x-ray crystallography, are defined as those for which the atomic coordinates of 2 or more of the main chain atoms of a particular amino acid residue of the precursor carbonyl hydrolase and *B. amyloliquefaciens* subtilisin (N on N, CA on CA, C on C, and O on O) are within 0.13 nm and preferably 0.1 nm after alignment. Alignment is achieved after the best model has been oriented and positioned to give the maximum overlap of atomic coordinates of non-hydrogen protein atoms of the carbonyl hydrolase in question to the *B. amyloliquefaciens* subtilisin. The best model is the crystallographic model giving the lowest R factor for experimental diffraction data at the highest resolution available.

$$R \text{ factor} = \frac{\sum_{h}||Fo(h)|-|Fc(h)||}{\sum_{h}|Fo(h)|}$$

Equivalent residues which are functionally analogous to a specific residue of *B. amyloliquefaciens* subtilisin are defined as those amino acids of the precursor carbonyl hydrolases which may adopt a conformation such that they either alter, modify or contribute to protein structure, substrate binding or catalysis in a manner defined and attributed to a specific residue of the *B. amyloliquefaciens* subtilisin as described herein. Further, they are those residues of the precursor carbonyl hydrolase (for which a tertiary structure has been obtained by x-ray crystallography), which occupy an analogous position to the extent that although the main chain atoms of the given residue may not satisfy the criteria of equivalence on the basis of occupying a homologous position, the atomic coordinates of at least two of the side chain atoms of the residue lie with 0.13nm of the corresponding side chain atoms of *B. amyloliquefaciens* subtilisin. The three dimensional structures would be aligned as outlined above.

Some of the residues identified for substitution are conserved residues whereas others are not. In the case of residues which are not conserved, the replacement of one or more amino acids is limited to substitutions which produce a mutant which has an amino acid sequence that does not correspond to one found in nature. In the case of conserved residues, such replacements should not result in a naturally occurring sequence. The subtilisin mutants of the present invention include the mature forms of subtilisin mutants as well as the pro- and prepro-forms of such subtilisin mutants. The prepro-forms are the preferred construction since this facilitates the expression, secretion and maturation of the subtilisin mutants.

"Prosequence" refers to a sequence of amino acids bound to the N-terminal portion of the mature form of a subtilisin which when removed results in the appearance of the "mature" form of the subtilisin. Many proteolytic enzymes are found in nature as translational proenzyme products and, in the absence of post-translational processing, are expressed in this fashion. The preferred prosequence for producing subtilisin mutants, specifically subtilisin BPN' mutants, is the putative prosequence of *B. amyloliquefaciens* subtilisin although other subtilisin prosequences may be used.

A "signal sequence" or "presequence" refers to any sequence of amino acids bound to the N-terminal portion of a subtilisin or to the N-terminal portion of a prosubtilisin which may participate in the secretion of the mature or pro forms of the subtilisin. This definition of signal sequence is a functional one, meant to include all those amino acid sequences, encoded by the N-terminal portion of the subtilisin gene or other secretable carbonyl hydrolases, which participate in the effectuation of the secretion of subtilisin or other carbonyl hydrolases under native conditions. The present invention utilizes such sequences to effect the secretion of the subtilisin mutants as defined herein.

A "prepro" form of a subtilisin mutant consists of the mature form of the subtilisin having a prosequence operably linked to the amino-terminus of the subtilisin and a "pre" or "signal" sequence operably linked to the amino terminus of the prosequence.

"Expression vector" refers to a DNA construct containing a DNA sequence which is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid" and "vector" are sometimes used interchangeably as the plasmid is the most commonly used form of vector at present. However, the invention is intended to include such other forms of expression vectors which serve equivalent functions and which are, or become, known in the art.

The "host cells" used in the present invention generally are procaryotic or eucaryotic hosts which preferably have been manipulated by the methods disclosed in EPO Publication No. 0130756 or 0251446 or U.S. Pat. No. 5,371,008 to render them incapable of secreting enzymatically active endoprotease. A preferred host cell for expressing subtilisin is the Bacillus strain BG2036 which is deficient in enzymatically active neutral protease and alkaline protease (subtilisin). The construction of strain BG2036 is described in detail in EPO Publication No. 0130756 and further described by Yang, M. Y., et al. (1984) *J. Bacteriol.* 160:15–21. Such host cells are distinguishable from those disclosed in PCT Publication No. 03949 wherein enzymatically inactive mutants of intracellular proteases in *E. coli* are disclosed. Other host cells for expressing subtilisin include *Bacillus subtilis* var. I168 (EPO Publication No. 0130756).

Host cells are transformed or transfected with vectors constructed using recombinant DNA techniques. Such transformed host cells are capable of either replicating vectors encoding the subtilisin mutants or expressing the desired subtilisin mutant. In the case of vectors which encode the pre or prepro form of the subtilisin mutant, such mutants, when expressed, are typically secreted from the host cell into the host cell medium.

"Operably linked" when describing the relationship between two DNA regions simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

The genes encoding the naturally-occurring precursor subtilisin may be obtained in accord with the general methods described in U.S. Pat. No. 4,760,025 or EPO Publication No. 0130756. As can be seen from the examples disclosed therein, the methods generally comprise synthesizing labeled probes having putative sequences encoding regions of the hydrolase of interest, preparing genomic libraries from organisms expressing the hydrolase, and screening the libraries for the gene of interest by hybridization to the probes. Positively hybridizing clones are then mapped and sequenced.

The cloned subtilisin is then used to transform a host cell in order to express the subtilisin. The subtilisin gene is then ligated into a high copy number plasmid. This plasmid replicates in hosts in the sense that it contains the well-known elements necessary for plasmid replication: a promoter operably linked to the gene in question (which may be supplied as the gene's own homologous promotor if it is recognized, i.e., transcribed, by the host), a transcription termination and polyadenylation region (necessary for stability of the mRNA transcribed by the host from the hydrolase gene in certain eucaryotic host cells) which is exogenous or is supplied by the endogenous terminator region of the subtilisin gene and, desirably, a selection gene such as an antibiotic resistance gene that enables continuous cultural maintenance of plasmid-infected host cells by growth in antibiotic-containing media. High copy number plasmids also contain an origin of replication for the host, thereby enabling large numbers of plasmids to be generated in the cytoplasm without chromosomal limitations. However, it is within the scope herein to integrate multiple copies of the subtilisin gene into host genome. This is facilitated by procaryotic and eucaryotic organisms which are particularly susceptible to homologous recombination.

Once the subtilisin gene has been cloned, a number of modifications are undertaken to enhance the use of the gene beyond synthesis of the naturally-occurring precursor subtilisin. Such modifications include the production of recombinant subtilisin as disclosed in U.S. Patent No. 5,371,008 or EPO Publication No. 0130756 and the production of subtilisin mutants described herein.

Mutant design and preparation

A number of structures have been solved of subtilisin with a variety of inhibitors and transition state analogs bound (Wright, C. S., Alden, R. A. and Kraut, J. [1969] *Nature*, 221:235–242; McPhalen, C. A. and James, N. G. [1988] *Biochemistry*, 27:6582–6598; Bode, W., Papamokos, E., Musil, D., Seemueller, U. and Fritz, M. [1986] *EMBO J.*, 5:813–818; and Bott, R., Ultsch, M., Kossiakoff, A., Graycar, T., Katz, B. and Power, S. [1988] *J. Biol. Chem.*, 263:7895–7906). One of these structures, FIG. 1 was used to locate residues that are in close proximity to side chains at the P1 and P2 positions from the substrate. Previous work had shown that replacement residues at positions 156 and 166 in the S1 binding site with various charged residues lead to improved specificity for complementary charged substrates (Wells, J. A., Powers, D. B., Bott, R. R., Graycar, T. P. and Estell, D. A. [1987a] *Proc. Natl. Acad. Sci. USA*, 84:1219–1223). Although longer range electrostatic effects of substrate specificity have been noted (Russell, A. J. and Fersht, A. R. [1987] *Nature*, 328:496–500) these were generally much smaller than local ones. Therefore it seemed reasonable that local differences in charge between subtilisin BPN' and the eukaryotic enzymes may account for the differences in specificity.

A detailed sequence alignment of 35 different subtilisins (Siezen, R. J., de Vos, W. M., Leunissen, A. M., and Dijkstra, B. W. [1991] *Prot. Eng.*, 4:719–737) allowed us to identify differences between subtilisin BPN' and the eukaryotic processing enzymes, KEX2, furin and PC2. Within the S1 binding pocket there are a number of charged residues that appear in the pro-hormone processing enzymes and not in subtilisin BPN' (Table 1A).

TABLE 1A

| | S1 subsite | | |
|---|---|---|---|
| | 125–131[a] | 151–157 | 163–168 |
| Subtilisin BPN' | SLGGPSG (SEQ ID NO: 3) | AAAGNEG (SEQ ID NO: 4) | ST-VGYP (SEQ ID NO: 5) |
| Kex2 | SWGPADD (SEQ ID NO: 6) | FASGNGG (SEQ ID NO: 7) | CNYDGYT (SEQ ID NO: 8) |
| Furin | SWGPEDD (SEQ ID NO: 9) | WASGNGG (SEQ ID NO: 10) | CNCDGYT (SEQ ID NO: 11) |
| PC2 | SWGPADD (SEQ ID NO: 6) | WASGDGG (SEQ ID NO: 12) | CNCDGYA (SEQ ID NO: 13) |

[a]numbering according to subtilisin BPN' sequence

For example, the eukaryotic enzymes have two conserved Asp residues at 130 and 131 as well as an Asp at 165 that is preceded by insertion of a Tyr or Cys. However, in the region from 151–157, subtilisin BPN' contains a Glu and the eukaryotes a conserved Gly.

In the S2 binding site there were two notable differences in sequence (Table 1B).

TABLE 1B

| | S2 subsite | |
|---|---|---|
| | 30–35 | 60–64 |
| Subtilisin BPN' | VIDSGI (SEQ ID NO: 14) | DNNSH (SEQ ID NO: 15) |
| KEX2 | IVDDGL (SEQ ID NO: 16) | SDDYH (SEQ ID NO: 17) |
| Furin | ILDDGI (SEQ ID NO: 18) | NDNRH (SEQ ID NO: 19) |
| PC2 | IMDDGI (SEQ ID NO: 20) | WFNSH (SEQ ID NO: 21) |

Subtilisin contains a Ser at position 33 whereas the pro-hormone processing enzymes contain Asp. There is not as clear a consensus in the region of 60–64, but one notable difference is at position 62. This side chain points directly at the P2 side chain (FIG. 1) as is Asn in subtilisin BPN', furin and PC2 but Asp in KEX2. Thus, not all substitutions were clearly predictive of the specificity differences.

A variety of mutants were produced to probe and engineer the specificity of subtilisin BPN' using oligonucleotides described in Table 2.

TABLE 2

Oligonucleotides used for site-directed mutagenesis on subtilisin.

| Mutant | Oligonucleotide | Specificity Pocket | Activity Expressed |
|---|---|---|---|
| S33D | 5'-GCGGTTATCGACG*A*CGGTATCGATTCT-3' (SEQ ID NO: 22) | S2 | + |
| S33K | 5'-GCGGTTATCGACAA*A*G*GTATCGATTCT-3' (SEQ ID NO: 23) | S2 | + |
| S33E | 5'-GCGGTTATCGACG*A*A*GGTATCGATTCT-3' (SEQ ID NO: 24) | S2 | + |
| N62D | 5'-CCAAGACAACG*ACTCTCACGGAA-3' (SEQ ID NO: 25) | S2 | + |
| N62S | 5'-CCAAGACAACAG*CTCTCACGGAA-3' (SEQ ID NO: 26) | S2 | + |
| N62K | 5'-CCAAGACAACAAA*TCTCACGGAA-3' (SEQ ID NO: 27) | S2 | + |
| G166D | 5'-CACTTCCGGCAGCTCG*T*C*G*ACAGTGGA*C*T ACCCTGGC.AAATA-3' (SEQ ID NO: 28) (Inserts Sal I site) | S1 | + |
| G166E | 5'-CACTTCCGGCAGCTCG*T*C*G*ACAGTGGA*GT ACCCTGGCAAATA-3' (SEQ ID NO: 29) (Inserts Sal I site) | S1 | + |
| G128P/P129A | 5'-TTAACATGAGCCTCGGCC*C*AG*CTA*G*C*GGT TCTGCTGCTTTA-3' (SEQ ID NO: 30) (Inserts Nhe I site) | S1 | − |
| G128P/P129A/ S130D/G131D | 5'-TTAACATGAGCCTCGGCC*C*C*G*CGG*A*TGA* TTCTGCTGCTTTAAA-3' (SEQ ID NO: 31) (Inserts Sac II site) | S1 | − |
| T164N/V165D | 5'-CGGCAGCTCAAGCA*A*C*G*A*T*GGCTAT*CCT | S1 | − |

TABLE 2-continued

Oligonucleotides used for site-directed mutagenesis on subtilisin.

| Mutant | Oligonucleotide | Specificity Pocket | Activity Expressed |
|---|---|---|---|
| T164Y/V165D | GGCAAATACCCTTCTGTCA-3'<br>(SEQ ID NO: 32) (Inserts BsaBI site)<br>5'-<br>CGGCAGCTCAAGCA*A*C*G*A*T*GGCTAT*CCT<br>GGCAAATACCCTTCTGTCA-3'<br>(SEQ ID NO: 32) (Inserts BsaBI site) | S1 | — |
| T164N-Y(insert)-V165D | 5'-<br>ACTTCCGGCAGCTCT*T*C*G*AA*C*T*A*C*G*A<br>*C*GGGTACCCTGGCAAATA-3'<br>(SEQ ID NO: 33) (Inserts BstBI site) | S1 | — |
| N62D/G166D | See individual mutations | S1/S2 | + |
| N62D/G166E | See individual mutations | S1/S2 | + |

*Asterisks indicate base changes from the pSS5 (wild-type) template.

After producing the mutant plasmids they were transformed into a protease deficient strain of *B. subtilis* (BG2036) that lacks an endogenous gene for secretion of subtilisin. These were then tested for protease activity on skim milk plates.

The first set of mutants tested were ones where segments of the S1 binding site were replaced with sequences from KEX2. None of these segment replacements produced detectable activity on skim milk plates even though variants of subtilisin whose catalytic efficiencies are reduced by as much as 1000-fold do produce detectable halos (Wells, J. A., Cunningham, B. C., Graycar, T. P. and Estell, D. A. (1986) *Philos. Trans. R. Soc. Lond. A.* 317:415–423). We went on to produce single residue substitutions that should have less impact on the stability. These mutants at positions 166 in the S1 site, and 33 and 62 in the S2 site, were chosen based on the modeling and sequence considerations described above. Fortunately all single mutants as well as combination mutants produced activity on skim milk plates and could be purified to homogeneity.

Kinetic analysis of variant subtilisins.

Figure 2:
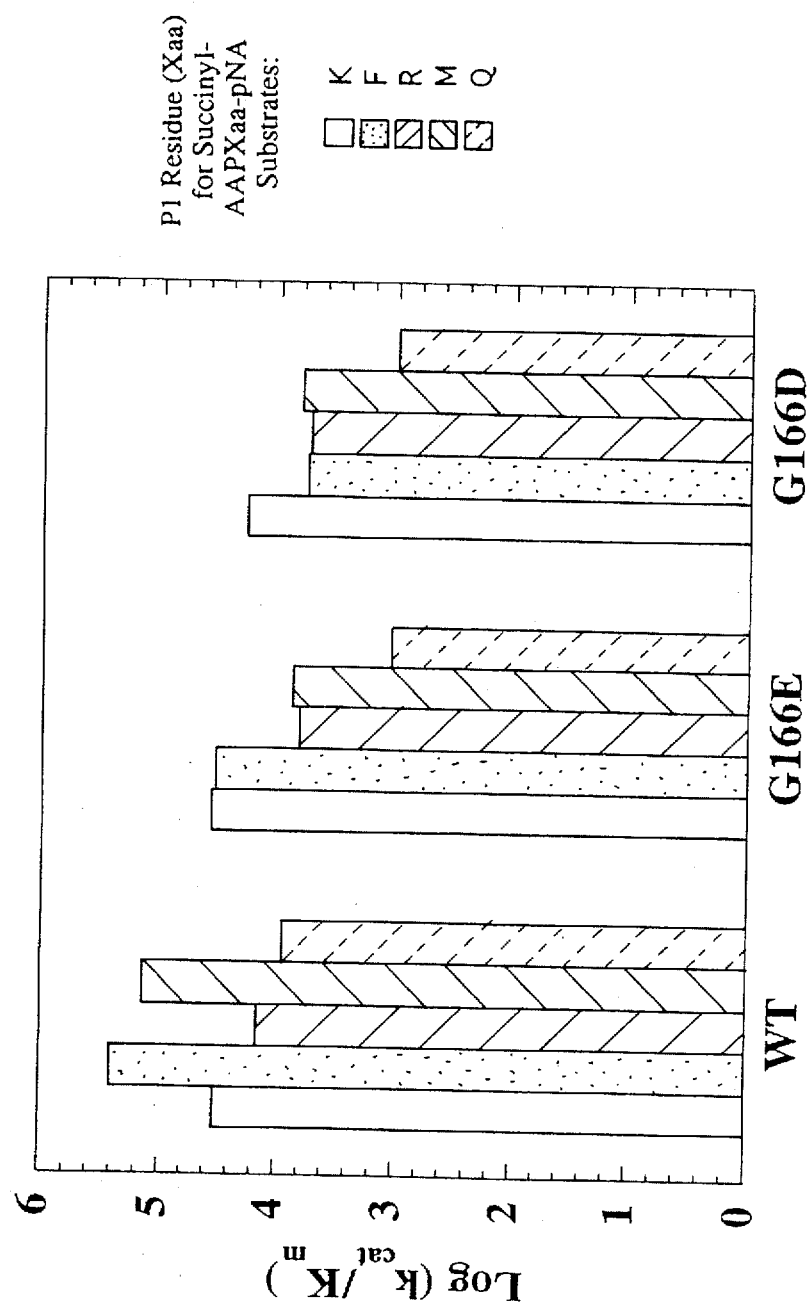
FIG. 2. Kinetic analysis of S1 binding site subtilisin mutants versus substrates having variable P1 residues. The kinetic constant $k_{cat}/K_m$ was determined from plots of initial rates versus substrate concentration for the tetrapeptide series succinyl-Ala-Ala-Pro-Xaa-pNa (SEQ ID NO: 69), were Xaa was Lys (SEQ ID NO: 58), Arg (SEQ ID NO: 59), Phe (SEQ ID NO: 56), Met (SEQ ID NO: 60) or Gln (SEQ ID NO: 61) (defined to the right of the plot).

To probe the effects of the G166E and G166D on specificity at the P1 position we used substrates having the form suc-AAPX-pna (SEQ ID NO: 69) where X was either Lys (SEQ ID NO: 58), Arg (SEQ ID NO: 59), Phe (SEQ ID NO: 56), Met (SEQ ID NO: 60) or Gln (SEQ ID NO: 61). The $k_{cat}/K_m$ values were determined from initial rate measurements and results reported in FIG. 2. Whereas the wild-type enzyme preferred Phe>Met>Lys>Arg>Gln, the G166E preferred Lys~Phe>Arg~Met>Gln, and G166D preferred Lys>Phe~Arg~Met>Gln. Thus, both the acidic substitutions at position 166 caused a shift in preference for basic residues as previously reported (Wells, J. A., Powers, D. B., Bott, R. R., Graycar, T. P. and Estell, D. A. (1987a), *Proc. Natl. Acad. Sci. USA* 84:1219–1223).

Figure 3:
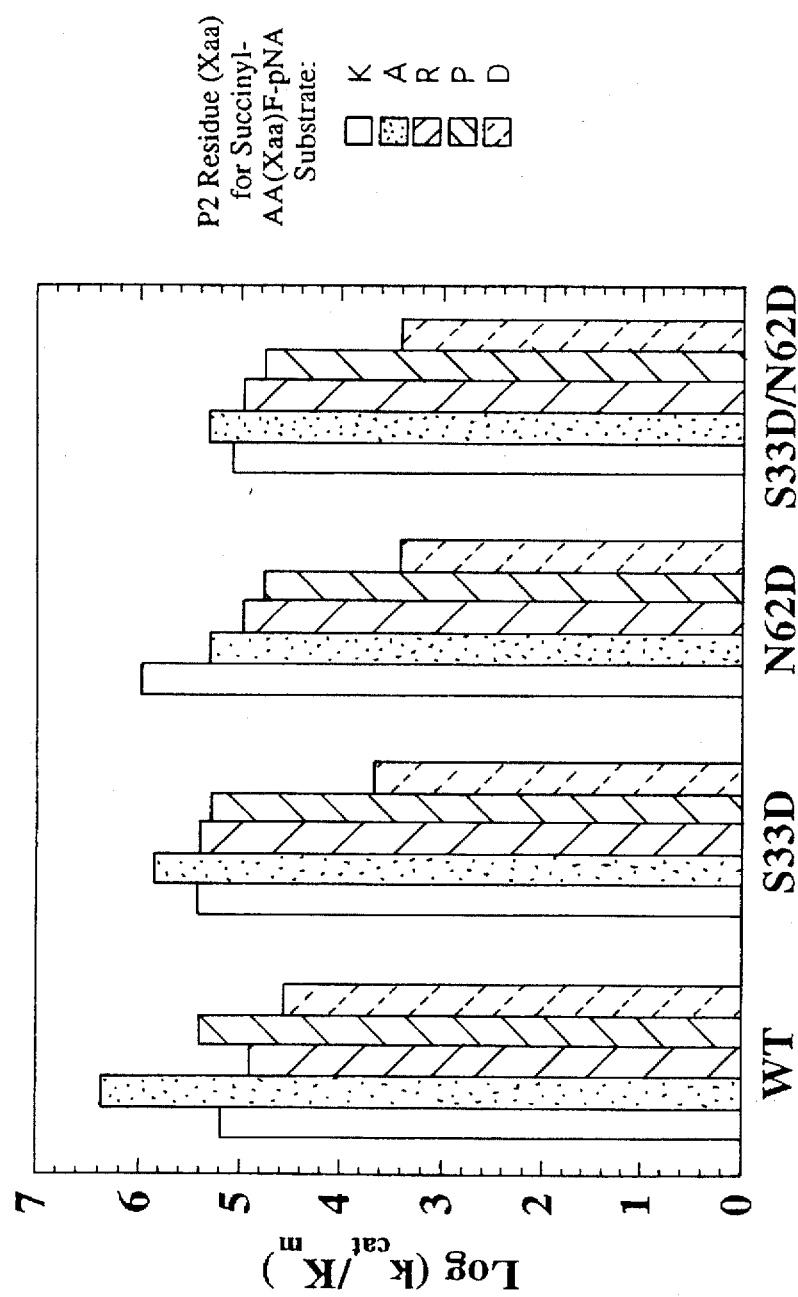
FIG. 3. Kinetic analysis of S2 binding site subtilisin mutants versus substrates having variable P2 residues. The kinetic constant $k_{cat}/K_m$ was determined from plots of initial rates versus substrate concentration for the tetrapeptide series succinyl-Ala-Ala-Xaa-Phe-pNa (SEQ ID NO: 70), were Xaa was Lys (SEQ ID NO: 62), Arg (SEQ ID NO: 64), Ala (SEQ ID NO: 63), Pro (SEQ ID NO: 56), or Asp (SEQ ID NO: 65) (defined on the right of the plot).

The effects of single and double substitutions in the S2 binding site were analyzed with substrates having the form, suc-Ala-Ala-X-Phe-pna and are shown in FIG. 3. At the P2 position the wild-type enzyme preferred Ala>Pro>Lys>Arg>Asp. In contrast, the S33D preferred Ala>Lys~Arg~Pro>Asp and the N62D preferred Lys>Ala>Arg>Pro>Asp. Although the effects were most dramatic for the N62D mutant, the S33D variant also showed significant improvement toward basic P2 residues and corresponding reduction in hydrolysis of the Ala and Asp P2 substrates. We then analyzed the double mutant, but found it exhibited the catalytic efficiency of the worse of the two single mutants for each of the substrates tested.

Figure 4:
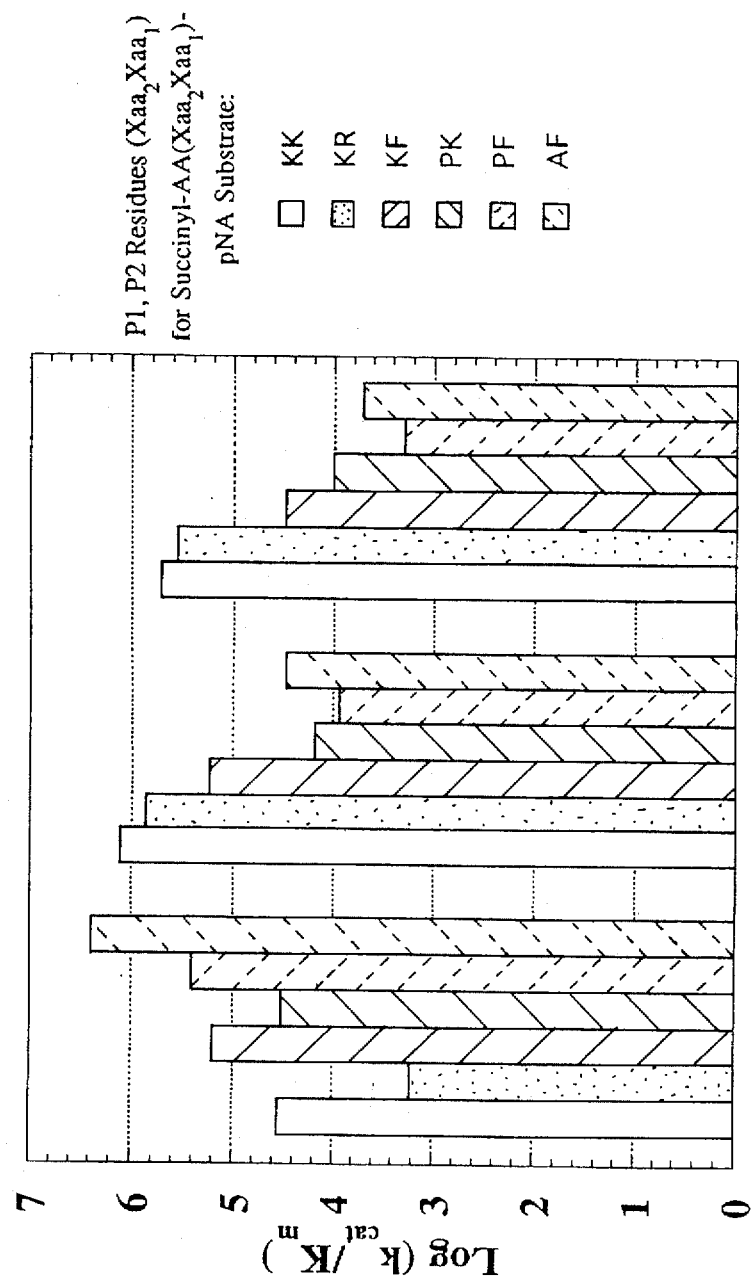
FIG. 4. Kinetic analysis of combined S1 and S2 binding site subtilisin mutants versus substrates having variable P1 and P2 residues. The kinetic constants $k_{cat}/K_m$ were determined from plots of initial rates versus substrate concentration for the tetrapeptide series succinyl-Ala-Ala-Xaa2-Xaa1-pNa (SEQ ID NO: 71), were Xaa$_2$-Xaa$_1$ was Lys-Lys (SEQ ID NO: 66), Lys-Arg (SEQ ID NO: 67), Lys-Phe (SEQ ID NO: 62), Pro-Lys (SEQ ID NO: 58), Pro-Phe (SEQ ID NO: 56), or Ala-Phe (SEQ ID NO: 63) (defined on the right of the plot).

Despite the less than additive effects seen for the two charged substitutions in the S2 site, we decided to combine the best S2 site variant (N62D) with either of the acidic substitutions in the S1 site. The two double mutants, N62D/G166E and N62D/G166D, were analyzed with substrates having the form, suc-AAXX-pna (SEQ ID NO: 71) where XX was either KK (SEQ ID NO: 66), KR (SEQ ID NO: 67), KF (SEQ ID NO: 62), PK (SEQ ID NO: 58), PF (SEQ ID NO: 56) or AF (SEQ ID NO: 63)(FIG. 4). The wild-type preference was AF>PF~KF>KK~PK>KR, whereas the double mutants had the preference KK>KR>KF>PK~AF>PF. Thus for the double mutants there was a dramatic improvement toward cleavage of dibasic substrates and away from cleaving the hydrophobic substrates.

The greater than additive effect (or synergy) of these mutants can be seen from ratios of the catalytic efficiencies for the single and multiple mutants. For example, the G166E variant cannot distinguish Lys from Phe at the P1 position. Yet the N62D/G166E variant cleaves the Lys-Lys substrate about 8 times faster than the Lys-Phe substrate. Similarly the G166D cleaves the Lys P1 substrate about 3 times faster than the Phe P1 substrate, but the N62D/G166D double mutant cleaves a Lys-Lys substrate 18 times faster than a Lys-Phe substrate. Thus, as opposed to the reduction in specificity seen for the double mutant in the S2 site, the S1-S2 double mutants enhance specificity for basic residues. It is possible that these two sites bind the dibasic substrates in a cooperative manner analogous to a chelate effect.

Substrate phage selection and cleavage of a fusion protein

Subtilisin has the capability to bind substrates from the P4 to P3' positions (McPhalen, C. A. and James, N. G. (1988) *Biochemistry* 27:6582–6598 and Bode, W., Papamokos, E., Musil, D., Seemueller, U. and Fritz, M. (1986) *EMBO J.* 5:813–818). Given this extensive binding site and the apparent cooperative nature in the way the substrate can bind the enzyme we wished to explore more broadly the substrate preferences for the enzyme. To do this we utilized a method we call substrate phage selection (Matthews, D. J., Goodman, L. J., Gorman, C. M., and Wells, J. A. (1994) *Protein Science* 3:1197–1205 and Matthews, D. J. and Wells, J. A. (1993) *Science* 260:1113–1117). In this method a five-residue substrate linker that was flanked by di-glycine residues is inserted between an affinity domain (in this case a high affinity variant of hGH) and the carboxy-terminal domain of gene III, a minor coat protein displayed on the surface of the filamentous phage, M13. The five residue substrate linker is fully randomized to generate a library of $20^5$ different protein sequence variants. These are displayed on the phage particles which are allowed to bind to the hGHbp. The protease of interest is added and if it cleaves the phage particle at the substrate linker it will release that particle. The particles released by protease treatment can be propagated and subjected to another round of selection to further enrich for good protease substrates. Sequences that are retained can also be propagated to enrich for poor protease substrates. By sequencing the isolated phage genes at the end of either selection one can identify good and poor substrates for further analysis.

We chose to focus on the subtilisin BPN' variant N62D/G166D as it was slightly better at discriminating the synthetic dibasic substrates from the others. We subjected the substrate phage library to nine rounds of selection with the subtilisin variant and isolated clones that were either increasingly sensitive or resistant to cleavage. Of twenty-one clones sequenced from the sensitive pool eighteen contained dibasic residues, eleven of which had the substrate linker sequence Asn-Leu-Met-Arg-Lys (SEQ ID NO: 35) (Table 3).

TABLE 3

Substrate phage sequences sensitive or resistant to N62D/G166D subtilisin from a GG-xxxxx-GG library after 9 rounds of selection*.

| Protease Sensitive Pool | | |
|---|---|---|
| No Basic Sites (0) | Monobasic Sites (3) | Dibasic Sites (18) |
| | NLTAR(3) (SEQ ID NO: 34) | NLMRK(11)(SEQ ID NO: 35) TASRR(4)(SEQ ID NO: 36) LTRRS(SEQ ID NO: 37) ALSRK(SEQ ID NO: 38) LMLRK(SEQ ID NO: 39) |

| Protease Resistant Pool | | |
|---|---|---|
| No Basic Sites (7) | Monobasic Sites (2) | Dibasic Sites (1) |
| ASTHF (SEQ ID NO: 40) IQQQY (SEQ ID NO: 43) QGELP (SEQ ID NO: 45) APDPT (SEQ ID NO: 46) QLLEH (SEQ ID NO: 47) VNNNH (SEQ ID NO: 48) AQSNL (SEQ ID NO: 49) | QKPNF (SEQ ID NO: 41) RPGAM (SEQ ID NO: 44) | RKPTH(SEQ ID NO: 42) |

*Numbers in parentheses indicate the number of times a particular DNA sequence was isolated.

Three (3) of the sensitive sequences were monobasic, Asn-Leu-Thr-Ala-Arg (SEQ ID NO: 34). It is known that subtilisin has a preference for hydrophobic residues at the P4 position. If these and the other selected substrates were indeed cleaved after the last basic residue they all would have a Leu, Met or Ala at the P4 position. Almost no basic residues were isolated in the protease resistant pool and those that were had a Pro following the mono- or dibasic residue. It is known that subtilisin does not cleave substrates containing Pro at the P1' position (Carter, P., Nilsson, B., Burnier, J., Burdick, D. and Wells, J. A. [1989] *Proteins: Struct., Funct., Genet.* 6:240–248). Thus, di-basic substrates where highly selected and these had the additional feature of Leu, Met or Ala at the P4 position.

We wished to analyze how efficiently the most frequently selected sequences were cleaved in the context of a fusion protein. For this we applied an alkaline phosphatase-fusion protein assay (Matthews, D. J., Goodman, L. J., Gorman, C. M., and Wells, J. A. [1994] *Protein Science* 3:1197–1205 and Matthews, D. J. and Wells, J. A. [1993] *Science* 260:1113–1117). The hGH substrate linker domains were excised from the phage vector by PCR and fused in front of the gene for *E. coli* AP. The fusion protein was expressed and purified on an hGH receptor affinity column. The fusion protein was bound to the hGH receptor on a plate and treated with the subtilisin variant. The rate of cleavage of the fusion protein from the plate was monitored by collecting soluble fractions as a function of time and assaying for AP activity (FIG. 5). The most frequently isolated substrate sequence, Asn-Leu-Met-Arg-Lys (SEQ ID NO: 35) was cleaved about ten times faster than the next most frequently isolated clones (Thr-Ala-Ser-Arg-Arg (SEQ ID NO: 50) and Asn-Leu-Thr-Ala-Arg (SEQ ID NO: 34)). We also tested the dibasic sequence isolated from the resistant pool, namely Arg-Lys-Pro-Thr-His (SEQ ID NO: 42). We observed no detectable cleavage above background for this substrate during the assay.

Cleavage of a Fusion Proteins With Subtilisin Variants

A fusion protein is any polypeptide that contains within it an affinity domain (AD) that usually aids in protein purification, a protease cleavage sequence or substrate linker (SL), which is cleaved by a protease and a protein product of interest (PP). Such fusion proteins are generally expressed by recombinant DNA technology. The genes for fusion proteins are designed so that the SL is between the AD and PP. These usually take the form AD-SL-PP such that the domain closest to the N-terminus is AD and PP is closest to the C-terminus.

Examples of AD would include, glutathione-S-transferase which binds to glutathione, protein A (or derivatives or fragments thereof) which binds IgG molecules, poly-histidine sequences, particularly (His)$_6$ (SEQ ID NO: 51) that bind metal affinity columns, maltose binding protein that binds maltose, human growth hormone that binds the human growth hormone receptor or any of a variety of other proteins or protein domains that can bind to an immobilized affinity support with an association constant (Ka) of >10$^5$ M$^{-1}$.

The SL can be any sequence which is cleaved by the N62D/G166D subtilisin variant but preferably ones with di-basic residues. The SL should be at least four residues and preferably contain a large hydrophobic residue at P4 (such as Leu or Met) and dibasic residues at P2 and P1 (such as Arg and Lys). A particularly good substrate is Leu-Met-Arg-Lys- (SEQ ID NO: 52), but a variety of other sequences may work including Ala-Ser-Arg-Arg (SEQ ID NO: 50) and even Leu-Thr-Ala-Arg (SEQ ID NO: 53). It is often useful that the SL contain a flexible segment on its N-terminus to better separate it from the AD and PP. Such sequences include Gly-Pro-Gly-Gly (SEQ ID NO: 54) but can be as simple as Gly-Gly or Pro-Gly. Thus, an example of a particularly good SL would have the sequence Gly-Pro-Gly-Gly-Leu-Met-Arg-Lys (SEQ ID NO: 55). This sequence would be inserted between the AD and PP domains.

The PP can be virtually any protein or peptide of interest but preferably should not have a Pro, Ile, Thr, Val, Asp or Glu as its first residue (P1'), or Pro or Gly at the second residue (P2') or Pro at the third residue (P3'). Such residues are poor substrates for the enzyme and may impair the ability of the N62D/G166D subtilisin variant to cleave the SL sequence.

The conditions for cleaving the fusion protein are best done in aqueous solution, although it should be possible to immobilize the enzyme and cleave the soluble fusion protein. It may also be possible to cleave the fusion protein as it remains immobilized on a solid support (e.g. bound to the solid support through AD) with the soluble N62D/G166D subtilisin variant. It is preferable to add the enzyme to the fusion protein so that the enzyme is less than one part in 100 (1:100) by weight. A good buffer is 10–50 mM Tris (pH 8.2) in 10 mM NaCl. A preferable temperature is about 25° C. although the enzyme is active up to 65° C. The extent of cleavage can be assayed by applying samples to SDS-PAGE. Generally suitable conditions for using the subtilisin variants of this invention do not depart substantially from those known in the art for the use of other subtilisins.

EXAMPLES

In the examples below and elsewhere, the following abbreviations are employed: subtilisin BPN', subtilisin from *Bacillus amyloliquefaciens*; Boc-RVRR-MCA (SEQ ID NO: 73), N-t-butoxy carbonyl-arginine-valine-arginine-arginine-7-amido-4-methyl coumarin (SEQ ID NO: 73); suc-Ala-Ala-Pro-Phe-pna (SEQ ID NO: 56), N-succinyl-alanine-alanine-proline-phenylalanyl-p-nitroanalide (SEQ ID NO: 56); hGH, human growth hormone; hGHbp, extracellular domain of the hGH receptor; PBS, phosphate buffered saline; AP, alkaline phosphatase;

Example 1
Construction and Purification of Subtilisin Mutants.

Site-directed mutations were introduced into the subtilisin BPN' gene cloned into the phagemid pSS5 (Wells, J. A., Ferrari, E., Henner, D. J., Estell, D. A. and Chen, E. Y. [1983] *Nucl. Acids Res.* 11:7911–7929). Single-stranded uracil-containing pSS5 template was prepared and mutagenesis performed using the method of Kunkel (Kunkel, T. A., Bebenek, K and McClary, J. [1991] *Methods Enzymol.* 204:125–139). For example, the synthetic oligonucleotide N62D, (5'-CCAAGACAACG*ACTCTCACGGAA-3') (SEQ ID NO: 25)

in which the asterisk denotes a mismatch to the wild-type sequence, was used to construct the N62D mutant. The oligonucleotide was first phosphorylated at the 5' end using T4 polynucleotide kinase according to a described procedure (Sambrook, J., Fritsch, E. F., and Maniatis, T. (1989) in "Molecular Cloning: A Laboratory Manual," Second Edition, Cold Spring Harbor, N.Y.). The phosphorylated oligonucleotide was annealed to single-stranded uracil-containing pSS5 template, the complementary DNA strand was filled in with deoxynucleotides using T7 polynucleotide kinase, and the resulting nicks ligated using T4 DNA ligase according to a previously described procedure (Sambrook, J., Fritsch, E. F., and Maniatis, T. (1989) in "Molecular Cloning: A Laboratory Manual," Second Edition, Cold Spring Harbor, N.Y.). Heteroduplex DNA was transformed into the *E. coli* host JM101(Yanish-Perron, C., Viera, J., and Messing, J. (1985) Gene 33: 103–199), and putative mutants were confirmed by preparation and dideoxy nucleotide sequencing of single stranded DNA (Sanger, F., Nicklen, S. and Coulson, A. R. (1977) *Proc. Natl. Acad. Sci. USA* 74:5463–5467) according to the Sequenase® protocol (USB Biochemicals). Mutant single-stranded DNA was then retransformed into JM101 cells and double stranded DNA prepared according to a previously described procedure (Sambrook, J., Fritsch, E. F., and Maniatis, T. (1989) in "Molecular Cloning: A Laboratory Manual," Second Edition, Cold Spring Harbor, N.Y.). For other mutations also requiring the use of one primer, the oligonucleotides used are listed in Table 2. For several of these oligonucleotides, additional silent mutations emplacing new restriction sites were simultaneously introduced to provide an alternative verification of mutagenesis.

To construct the double mutants N62D/G166D, and N62D/G166E, pSS5 DNA containing the N62D mutation was produced in single-stranded uracil-containing form using the Kunkel procedure (Kunkel, T. A., Bebenek, K and McClary, J. (1991) *Methods Enzymol.* 204, 125–139). This mutant DNA was used as template for the further introduction of the G166D or G166E mutations, using the appropriate oligonucleotide primers (see sequences in Table 2), following the procedures described above.

For expression of the subtilisin BPN' mutants, double stranded mutant DNA was transformed into a protease-deficient strain (BG2036) of *Bacillus Subtilis* (Yang, M. Y., Ferrari, E. and Henner, D. J. (1984) *Journal of Bacteriology* 160:15–21) according to a previous method (Anagnostopolouus, C. and Spizizen, J. (1961) *Journal of Bacteriology* 81:741–746) in which transformation mixtures were plated out on LB plus skim milk plates containing 12.5 μg/mL chloramphenicol. The clear halos indicative of skim milk digestion surrounding transformed colonies were noted to roughly estimate secreted protease activity.

The transformed BG2036 strains were cultured by inoculating 5 mL of 2xYT media (Miller, J. H., (1972) in "Experiments in Molecular Genetics," Cold Spring Harbor, N.Y.) containing 12.5 μg/mL chloramphenicol and 2 mM $CaCl_2$ at 37° C. for 18–20 h, followed by 1:100 dilution in $CaCl_2$ at 37° C. for the same medium and growth in shake flasks at 37° C. for 18–22 h with vigorous aeration. The cells were harvested by centrifugation (6000 g, 15 min, 4° C.), and to the supernatant 20 mM (final) $CaCl_2$ and one volume of ethanol (–20° C.) were added. After 30 min at 4° C., the solution was centrifuged (12,000 g, 15 min., 4° C.), and one volume of ethanol (–20° C.) added to the supernatant. After 2 h at –20° C., the solution was centrifuged (12,000g, 15 min, 4° C.) and the pellet resuspended in and dialyzed against MC (25 mM 2-[N-Morpholino]ethanesulfonic acid (MES), 5 mM $CaCl_2$ at pH 5.5) overnight at 4° C. The dialysate was passed through a 0.22 μm syringe filter and loaded onto a mono-S cation exchange column run by an FPLC system (Pharmacia Biotechnology). The column was washed with 20 volumes of MC and mutant subtilisin eluted over a linear gradient of zero to 0.15M NaCl in MC, all at a flow rate of 1 mL/min. Peak fractions were recovered and the subtilisin mutant quantitated by measuring the absorbance at 280 nm ($E_{280}$ 0.1%=1.17) (Matsubara, H.; Kasper, C B.; Brown, D. M.; and Smith, E. L. (1965) *J. Biol. Chem.*, 240:1125–1130.).

Example 2
Kinetic Characterizations

Subtilisins were assayed by measuring the initial rates of hydrolysis of p-nitroanilide tetrapeptide substrates in 0.4 mL 20 mM Tris-Cl pH 8.2, 4 % (v/v) dimethyl sulfoxide at (25±0.2)° C. as described previously (Estell, D. A., Graycar, T. P., Miller, J. V., Powers, D. B., Burnier, J. P., Ng, P. G. and Wells, J. A. [1986] *Science* 233:659–663). Enzyme concentrations $[E]_0$ were determined spectrophotometrically using $E_{280}$ nm 0.1%=1.17 (Matsubara, H.; Kasper, C B.; Brown, D. M.; and Smith, E. L. (1965) *J. Biol. Chem.*, 240:1125–1130.), and were typically 5–50 nM in reactions. Initial rates were determined for nine to twelve different substrate concentrations over the range of 0.001–2.0 mM. Plots of initial rates (v) versus substrate concentration [S] were fitted to the Michaelis-Menton equation.

$$v = \frac{k_{cat}[E]_0([S])}{K_m + [S]}$$

to determine the kinetic constants $k_{cat}$ and $K_m$ (Fersht, A. in "Enzyme Structure and Mechanism", Second edition, Freeman and Co., N.Y.) using the program Kaleidagraph (Synergy Software, Reading, Pa.).

Example 3

Substrate Phage

Substrate phage selections were performed as described by Matthews and Wells (Matthews, D. J. and Wells, J. A. (1993) *Science* 260:1113–1117), with minor modifications. Phage sorting was carried out using a library in which the linker sequence between the gene III coat protein and a tight-binding variant of hGH was GPGGX$_5$GGPG (SEQ ID NO: 57). The library contained 2×10$^6$ independent transformants. Phage particles were pre pare d by infecting 1 mL of log phase 27C7 (F'/tet$^R$/Ompt[/degP$^-$) *Escherichia coli* with ~10$^8$ library phage for 1 h at 37° C., followed by 18–24 h of growth in 25 mL 2YT medium containing 10$^{10}$ M13K07 helper phage and 50 μg/mL carbenicillin at 37° C. Wells of a 96-well Nunc Maxisorb microtiter plate were coated with 2 μg/mL of hGHbp in 50 mM NaHCO$_3$ at pH 9.6 overnight at 4° C. and blocked with PBS (10 mM sodium phosphate at pH 7.4 nd 150 mM NaCl) containing 2.5% (w/v) skim milk for 1 h at room temperature. Between 10$^{11}$ and 10$^{12}$ phage in 0.1 mL 10 mM tris-Cl (pH 7.6), 1 mM EDTA, and 100 mM NaCl were incubated in the wells at room temperature for 2 h with gentle agitation. The plate was washed first with 20 rinses of PBS plus 0.05% Tween 20 and then twice with 20 mM tris-Cl at pH 8.2. The N62D/G166D subtilisin was added in 0.1 mL of 20 mM tris-Cl at pH 8.2 and protease sensitive phage were eluted after a variable reaction time. The concentration of protease and incubation times for elution of sensitive phage were decreased gradually over the course of sorting procedure to increase selectivity, with protease concentrations of 0.2 nM (rounds 1–3) and 0.1 nM (rounds 4–9), and reaction times of 5 min (rounds 1–6), 2.5 min (round 7), 40 s (round 8) and 20 s (round 9). Control wells in which no protease was added were also included in each round. For the resistant phage pool, the incubation time with protease remained constant at 5 min. The wells were then washed ten times with PBS plus 0.05% Tween 20 and resistant phage eluted by treatment with 0.1 mL of 0.2M glycine at pH 2.0 in PBS plus 0.05% Tween 20 for 1 min at room temperature. Protease sensitive and resistant phage pools were titered and used to infect log phase 27C7 cells for 1 h at 37° C., followed by centrifugation at 4000 rpm, removal of supernatant, and resuspension in 1 mL 2YT medium. The infected cells were then grown 18–24 h in the presence of helper phage as described above and the process repeated 9 times. Selected substrates were introduced into AP fusion proteins and assayed for relative rates of cleavage as described by Matthews and Wells (Matthews, D. J., Goodman, L. J., Gorman, C. M., and Wells, J. A. (1994) *Protein Science* 3:1197–1205 and Matthews, D. J. and Wells, J. A. (1993) *Science* 260:1113–1117), except that the cleavage reactions were performed in 20 mM Tris-Cl at pH 8.2.

The present invention has of necessity been discussed herein by reference to certain specific methods and materials. It is to be understood that the discussion of these specific methods and materials in no way constitutes any limitation on the scope of the present invention, which extends to any and all alternative materials and methods suitable for accomplishing the ends of the present invention.

All references cited herein are expressly incorporated by reference.

What is claimed is:

1. A subtilisin modified to have substrate specificity for peptide substrates having basic amino acids at the $P_2$ and $P_1$ positions of the substrate, said subtilisin having an Asp or Glu at an amino acid residue equivalent to Asn 62 and Gly 166 of the subtilisin having the amino acid sequence of SEQ ID NO: 74 naturally produced by *Bacillus amyloliquefaciens*.

2. The modified subtilisin of claim 1 having an Asp at an amino acid residue equivalent to Asn 62 of the subtilisin naturally produced by *Bacillus amyloliquefaciens*.

3. The modified subtilisin of claim 2 having a Glu at an amino acid residue equivalent to Gly 166 of the subtilisin naturally produced by *Bacillus amyloliquefaciens*.

4. The modified subtilisin of claim 2 having the amino acid sequence of the mature polypeptide provided in FIG. 6 (SEQ ID NO: 72).

5. An isolated nucleic acid molecule encoding the modified subtilisin of claim 1.

6. The nucleic acid molecule of claim 5 further comprising a promoter operably linked to the nucleic acid molecule.

7. An expression vector comprising the nucleic acid molecule of claim 6 operably linked to control sequences recognized by a host cell transformed with the vector.

8. A host cell transformed with the vector of claim 7.

9. A process of using the nucleic acid molecule encoding the subtilisin variant to effect production of the subtilisin variant comprising culturing the host cell of claim 8 under conditions suitable for expression of the subtilisin variant.

10. The process of claim 9 further comprising recovering the subtilisin variant from the host cell culture medium.

11. A method of using the modified subtilisin of claim 1 comprising contacting a fusion protein having a dibasic sequence with the modified subtilisin.

* * * * *